United States Patent
Sridhar et al.

(10) Patent No.: US 11,752,328 B2
(45) Date of Patent: Sep. 12, 2023

(54) NEUROMODULATION DEVICE

(71) Applicants: Galvani Bioelectronics Limited, Brentford Middlesex (GB); Case Western Reserve University, Cleveland, OH (US)

(72) Inventors: Arun Sridhar, Brentford Middlesex (GB); Alessandra Giarola, Brentford Middlesex (GB); Stephen J. Lewis, Cleveland, OH (US)

(73) Assignees: Galvani Bioelectronics Limited, Middlesex (GB); Case Western Reserve University, Cleveland, OH (US)

(*) Notice: Subject to any disclaimer, the term of this patent is extended or adjusted under 35 U.S.C. 154(b) by 146 days.

(21) Appl. No.: 16/471,473

(22) PCT Filed: Dec. 20, 2017

(86) PCT No.: PCT/EP2017/083854
§ 371 (c)(1),
(2) Date: Jun. 19, 2019

(87) PCT Pub. No.: WO2018/115141
PCT Pub. Date: Jun. 28, 2018

(65) Prior Publication Data
US 2020/0086109 A1    Mar. 19, 2020

Related U.S. Application Data

(60) Provisional application No. 62/436,666, filed on Dec. 20, 2016.

(51) Int. Cl.
*A61N 1/05* (2006.01)
*A61N 1/36* (2006.01)
*A61B 5/00* (2006.01)

(52) U.S. Cl.
CPC .......... *A61N 1/0514* (2013.01); *A61N 1/3611* (2013.01); *A61N 1/36146* (2013.01); *A61B 5/4818* (2013.01)

(58) Field of Classification Search
CPC .... A61N 1/0514; A61N 1/0551; A61N 1/326; A61N 1/3611; A61N 1/36117; A61N 1/36146; A61B 5/4818
(Continued)

(56) References Cited

U.S. PATENT DOCUMENTS

2005/0288730 A1    12/2005   Deem et al.
2011/0208173 A1*   8/2011    Sobotka ............ A61B 18/1492
                                                              606/20
(Continued)

FOREIGN PATENT DOCUMENTS

WO    WO 2016/072875 A1    5/2016

OTHER PUBLICATIONS

PCT/EP2017/083854, Feb. 20, 2018, International Search Report and Written Opinion.
(Continued)

*Primary Examiner* — Carl H Layno
*Assistant Examiner* — Jane C Kalinock
(74) *Attorney, Agent, or Firm* — Banner & Witcoff, Ltd.

(57) ABSTRACT

A neuromodulation apparatus for stimulating neural activity in a renal nerve of a patient is provided, the apparatus comprising a transducer Patient for applying a signal to the renal nerve so as to produce a physiological response. Methods of treating sleep apnoea are also provided, including methods using the neuromodulation apparatus.

18 Claims, 11 Drawing Sheets

Figure 1:
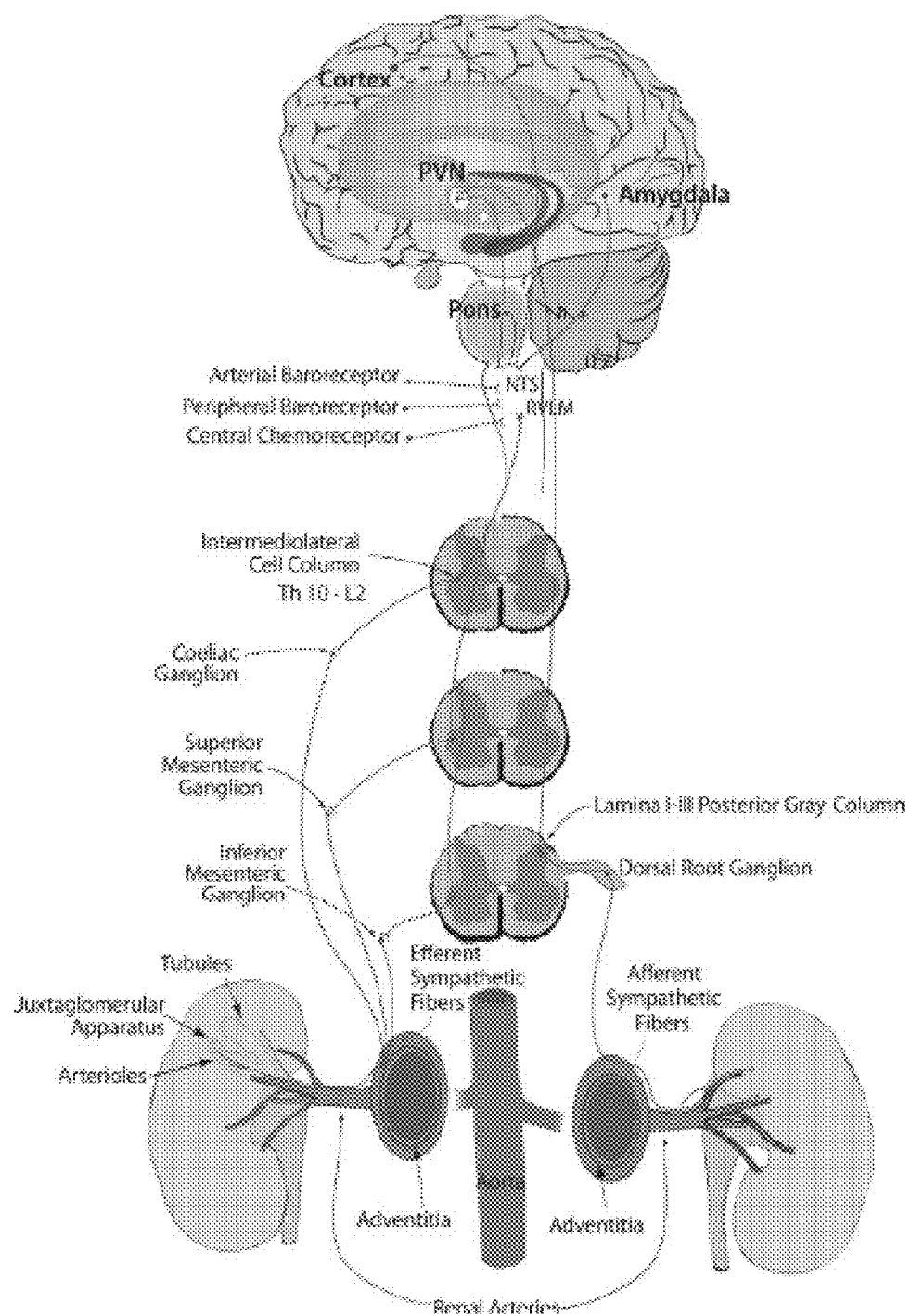

Neuromodulation device in accordance with an embodiment of the present disclosure Neuromodulation device in accordance with another embodiment of the present disclosure

(58) Field of Classification Search
USPC .......................................................... 607/42
See application file for complete search history.

(56) References Cited

U.S. PATENT DOCUMENTS

| | | | |
|---|---|---|---|
| 2016/0030740 A1* | 2/2016 | Mashiach | A61N 1/37211 |
| | | | 607/42 |
| 2016/0158542 A1 | 6/2016 | Ahmed | |
| 2017/0021168 A1* | 1/2017 | Yun | A61N 1/36117 |
| 2017/0095291 A1* | 4/2017 | Harrington | A61B 5/6852 |

OTHER PUBLICATIONS

Ciriello et al., Central projections of afferent renal fibers in the rat: an anterograde transport study of horseradish peroxidase., J Auton Nerv Syst. 8: 273-285, 1983.

Donovan et al., Localization of renal sensory neurons using the fluorescent dye technique ., Brain Res. 259: 119-122, 1983.

Weiss and Chowdhury, The renal afferent pathways in the rat: a pseudorabies virus study ., Brain Res. 812: 227-241, 1998.

Lappe et al., Selective destruction of renal afferent versus efferent nerves in rats., Am J Physiol. 249: R634-R637, 1985.

Stella A, Zanchetti A. Functional role of renal afferents. Physiol Rev. Jul. 1991;71(3):659-82. doi: 10.1152/physrev.1991.71.3.659. PMID: 1647536.

Bertog et al., Renal denervation for hypertension. JACC Cardiovasc Interv. 5: 249-258, 2012.

Koopman et al., Arthritis & Rheumatism, vol. 64, No. 10 (Supplement), page S195 (Abstract No. 451), Oct. 2012. "Pilot Study of Stimulation of the Cholinergic Antiinflammatory Pathway with an Implantable Vogus Nerve Stimulation Device in Patients with Rheumatoid Arthritis".

Vuckovic et al 9th Annual Conference of the International FES Society Sep. 2004.

Accornero et al, Selective Activation of peripheral nerve fibre groups of different diameter by triangular shaped stimulus pulses ., J. Physiol. (1977), 273, pp. 539-560.

Foss et al., A novel method of selective ablation of afferent renal nerves by periaxonal application of capsaicin ., Am J Physiol Regul Integr Comp Physiol. 308: R112-R122, 2015.

Lewis et al., Cardiovascular effects of the N-methyl-D-aspartate receptor antagonist MK-801 in conscious rats ., Hypertension 13: 759-765, 1989.

May et al., Morphine has latent deleterious effects on the ventilatory responses to a hypoxic-hypercapnic challenge Open J Mol Integ Physiol. 3: 134-145, 2013.

Getsy et al., Enhanced non-eupneic breathing following hypoxic, hypercapnic or hypoxic-hypercapnic gas challenges in conscious mice ., Respir Physiol Neurobiol. 204: 147-59, 2014.

Smits et al., Activation of afferent renal nerves by intrarenal bradykinin in conscious rats ., Am J Physiol. 247: R1003-R1008, 1984.

Dempsey et al., Pathophysiology of sleep apnea ., Physiol Rev. 90: 47-112, 2010.

Felder, Excitatory and inhibitory interactions among renal and cardiovascular afferent nerves in dorsomedial medulla ., Am J Physiol. 250: R580-R588, 1986.

Fellmann et al., Murine models for pharmacological studies of the metabolic syndrome ., Pharmacol Ther. 137: 331-340, 2013.

Wang et al., Leptin- and leptin receptor-deficient rodent models: relevance for human type 2 diabetes ., Curr Diabetes Rev. 10:131-145, 2014.

Gao and Zheng, Animal models of diabetic neuropathic pain ., Exp Clin Endocrinol Diabetes 122: 100-106, 2014.

Iwasaki et al., Determinants of atrial fibrillation in an animal model of obesity and acute obstructive sleep apnea ., Heart Rhythm 9: 1409-1416, 2012.

Renninger, Head-out plethysmography in safety pharmacology assessment., Curr Protoc Pharmacol. Chapter 10: Unit 10.11, 2006.

Ewert et al., Pharmacological validation of a telemetric model for the measurement of bronchoconstriction in conscious rats ., J Pharmacol Toxicol Methods 61: 219-229, 2010.

Wyss, J. M., and M. K. Donovan. A direct projection from the kidney to the brainstem. Brain Res. 298: 130-134, 1984.

\* cited by examiner

Neuromodulation device in accordance with an embodiment of the present disclosure Neuromodulation device in accordance with another embodiment of the present disclosure Neuromodulation device in accordance with another embodiment of the present disclosure

A

B

C

D

E

NEUROMODULATION DEVICE

RELATED APPLICATIONS

This application is a national stage filing under 35 U.S.C. § 371 of International Patent Application Serial No. PCT/EP2017/083854, filed Dec. 20, 2017, which claims the benefit under 35 U.S.C. § 119(e) of U.S. Provisional Application Ser. No. 62/436,666, filed Dec. 20, 2016, the entire contents of each of which is incorporated by reference herein in its entirety.

BACKGROUND

Sleep apnoea is a condition in which normal breathing is interspersed by episodes of complete ventilatory silence and/or erratic (non-eupnoeic) breathing. These episodes of sleep apnoea and erratic breathing typically occur during the rapid-eye movement (REM) phase of the sleep cycle. Symptoms of sleep apnoea include fatigue, cognitive impairment (for example slower reaction time, impaired memory), hypertension, and vision problems.

Sleep apnoea may be classified as central sleep apnoea or obstructive sleep apnoea, with many patients having both. Central sleep apnoea (CSA) is due to inadequate neural control of respiratory muscles and lack of respiratory drive. Obstructive Sleep Apnoea (OSA) is a disorder characterised by repetitive collapse and reopening of the upper airway during sleep, which impairs ventilation and can result in intermittent hypoxemia and hypercapnia. OSA is a multi-factorial disorder and the pathophysiological factors that contribute to OSA include reduced upper airway dilator muscle activity during sleep, upper airway anatomical features that vary from normal, insufficient ventilatory control and diminished lung volume. OSA has been shown to be a major risk factor for developing diabetes, hypertension, atrial fibrillation, heart failure and sudden death.

Ventilation is a neurally and mechanically active (inspiration) and passive (expiration) process. The involuntary control of breathing is driven by the respiratory neural network in the brainstem and is in part mediated via increased activity of diaphragmatic and chest-wall muscles (via increased drive from the phrenic and intercostal nerves).

Attempts to treat CSA have included diaphragmatic pacing. Such pacing uses a device which stimulates the phrenic nerve (motor nerve driving the diaphragm) via an intravascular lead. Attempts to treat OSA have included hypoglossal nerve stimulation, using a closed-loop reactive unit that triggers stimulation of the hypoglossal nerve upon detection of absence of chest movement (using an impedance sensor).

SUMMARY OF INVENTION

Among a variety of factors, the effectiveness of inspiration and expiration is critically-dependent on the patency and open-status (position of the tongue) of the upper airway. Therefore, the tongue (genioglossus) and orophayngeal muscles as well as motor drive to these muscles have a critical role in determining upper airway patency. The involuntary control of breathing can be modulated by (1) descending input from higher brain centres (e.g., prefrontal cortex, hypothalamus) into the brainstem to allow for adjustments in breathing that are required to match the physiological requirements of the body, and (2) peripheral chemoreceptors emanating from the carotid bodies (which continually sample arterial blood $pO_2$, pH and $pCO_2$ levels) to alert the brainstem respiratory control centres as to any changes in arterial blood-gas chemistry. The carotid bodies detect hypoxic episodes such as occur during sleep apnoea to trigger afferent signals that adjust central respiratory drive.

Anatomical mapping of afferent fibres of the rat kidney has identified the pathways traversed by these fibres including locations of their cell bodies in dorsal root ganglia (DRG) of the spinal cord.

Afferent nerves arising from the left kidney project ipsilaterally through dorsal roots T8-L2 with most fibres (>90%) confined to dorsal roots T10-L1. Afferent projections arising from the right kidney are found in dorsal roots T9-L1, with most fibres (>90%) in T9-T13. The central projections of many of these renal afferents terminate within the nucleus tractus solitarius (NTS) including medial and caudal sub-nuclei that control hemodynamic and ventilatory functions, respectively [Ciriello et al., J Auton Nerv Syst. 8: 273-285, 1983; Donovan et al., Brain Res. 259: 119-122, 1983; Weiss and Chowdhury, Brain Res. 812: 227-241, 1998; Lappe et al., Am J Physiol. 249: R634-R637, 1985, all of which are incorporated herein by reference]. Viral tracing studies indicate that primary sensory neurons innervating the kidney are found in the dorsal root ganglia in T8-L4 spinal cord levels ipsilateral to the kidney investigated. Kidney infection in the rat with PRV consistently infected cells in four CNS sites: ventrolateral medulla, A5 region of the pons, the caudal raphe nuclei-parapyramidal area and the paraventricular nucleus in the hypothalamus (Weiss and Chowdhury, 1998). Although the vital roles of the sub-types (e.g., mechanosensitve, chemosensitive) of renal afferents in the control of hemodynamic function is well established, virtually nothing is known about the role of renal afferents in the control of ventilation and expression of disordered breathing such as apnoeas [Stella and Zanchetti 1991, incorporated herein by reference].

The inventors identified that the renal nerve is a candidate for modulating physiological functions playing important roles in sleep apnoea. As demonstrated herein, stimulation of the renal nerve is able to induce improvements in a range of sleep apnoea associated functions, including airway resistance, and the frequency and duration of disordered apnoeic breaths.

Therefore, provided in a first aspect is a neuromodulation apparatus for stimulating neural activity in a renal nerve of a patient, the apparatus comprising: a transducer configured to apply a signal to a renal nerve of the patient; and a controller coupled to the transducer, the controller controlling the signal to be applied by each of the transducer, such that the signal increases neural activity in the nerve to produce a physiological response in the patient.

Provided in a second aspect is a method of treating sleep apnoea in a patient comprising: (i) implanting in the patient an apparatus according to the first aspect; (ii) positioning the transducer of the apparatus in signalling contact with a renal nerve of the patient; (iii) activating the apparatus.

Provided in a third aspect is a method of treating sleep apnoea in a patient, the method comprising applying a signal to a renal nerve of said patient to increase neural activity in said nerve in the patient. In certain embodiments the signal is applied by a neuromodulation apparatus comprising a transducer configured to apply the signal.

Provided in a fourth aspect is a neuromodulatory electrical waveform for use in treating sleep apnoea in a patient, wherein the waveform is an alternating current (AC) or direct current (DC) waveform having a frequency of about 0.5-50 Hz, optionally 0.5-25 Hz, optionally 1-10 Hz, optionally 1-5 Hz, optionally 2-2.5 Hz, such that, when applied to renal nerve the waveform stimulates neural signalling in the nerve.

Provided in a fifth aspect is use of a neuromodulation apparatus for treating sleep apnoea in a patient by stimulating neural activity in a renal nerve of the patient.

In a preferred embodiment of all aspects of the invention, the patient is a human.

DETAILED DESCRIPTION

Figures

FIG. 1: Diagram showing the innervation of the kidney, including the renal nerve. Picture taken from Bertog S C, Sobotka P A, Sievert H. Renal denervation for hypertension. JACC Cardiovasc Interv. 5: 249-258, 2012, incorporated herein by reference. NTS—solitary tract nucleus; PVN—paraventricular nucleus; RVLM—rostral ventrolateral medulla.

FIG. 2: Schematic drawings showing how apparatuses, devices and methods according to the invention can be put into effect.

Figure 3:
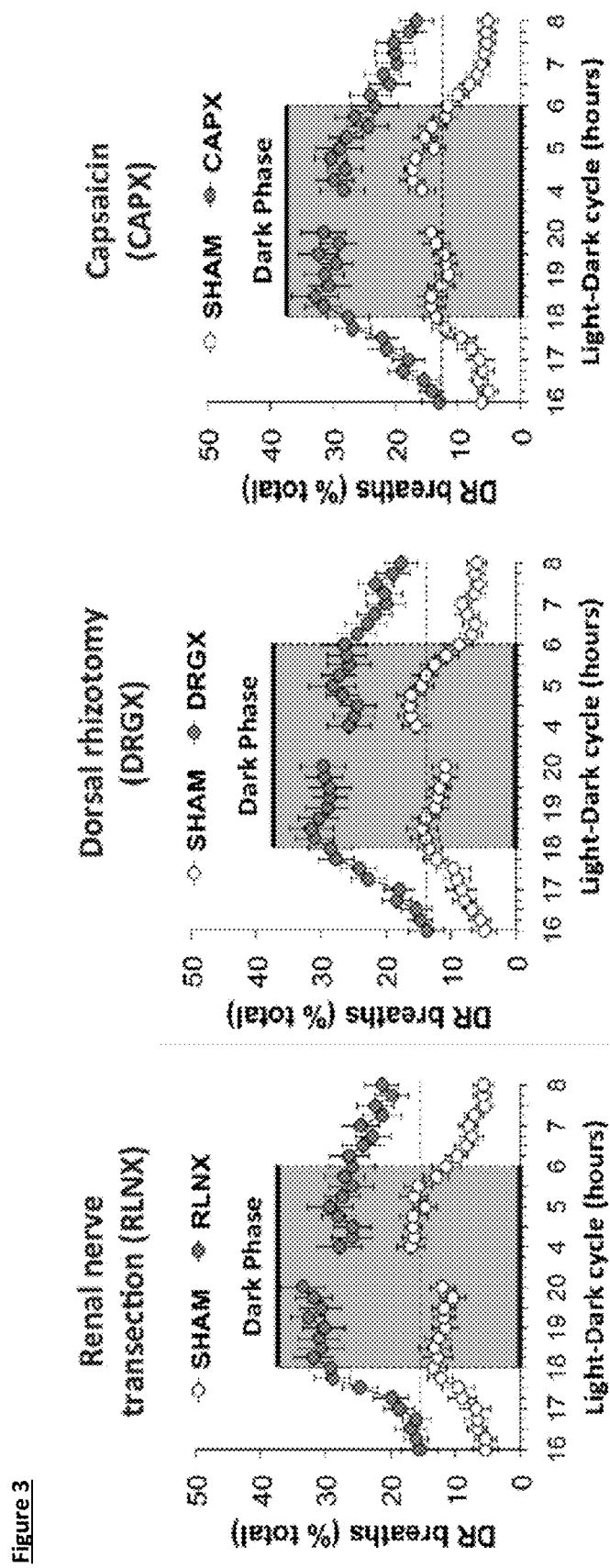

FIG. 3: Resting levels of disordered breathing (% of total time) in freely-moving Sprague-Dawley rats following renal nerve transection, dorsal rhizotomy or treatment with capsaicin compared to sham treated animals. There were 9 rats in each group. The data are presented as mean±SEM.

Figure 4:
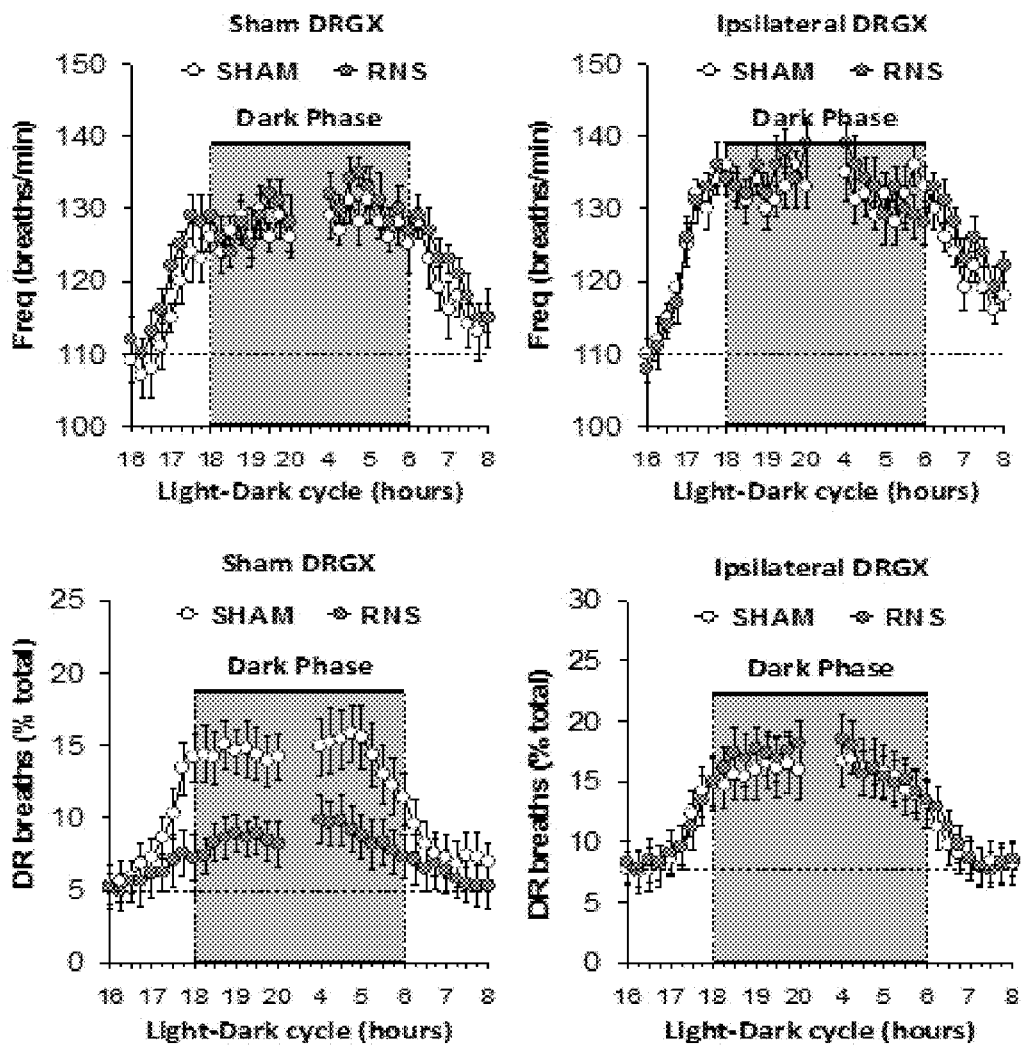

FIG. 4: Left renal nerve stimulation diminishes disordered breathing (% of total time) in freely-moving Sprague-Dawley rats. There were 9 rats in each group. The data are presented as mean±SEM.

Figure 5:
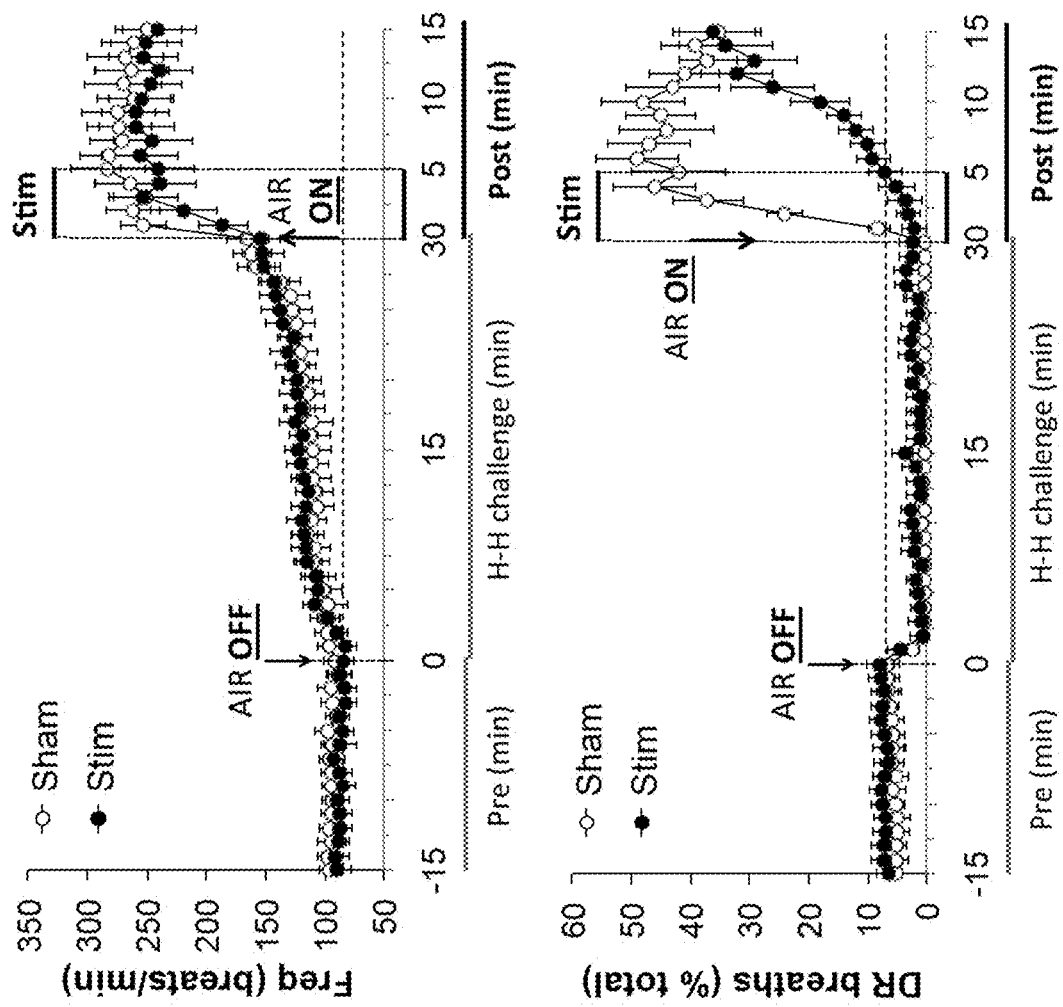

FIG. 5: Changes in frequency of breathing (top panel) and disordered breathing (DR breaths) before, during and following a hypoxic-hypercapnic challenge in Sprague-Dawley rats. The 5 min episodes of sham stimulation or bilateral 2.5 Hz electrical stimulation (0.1 mA, 0.5 msec) for 5 min of the renal nerves are shown. The data are presented as mean±SEM. There were 12 rats in each group.

Figure 6:
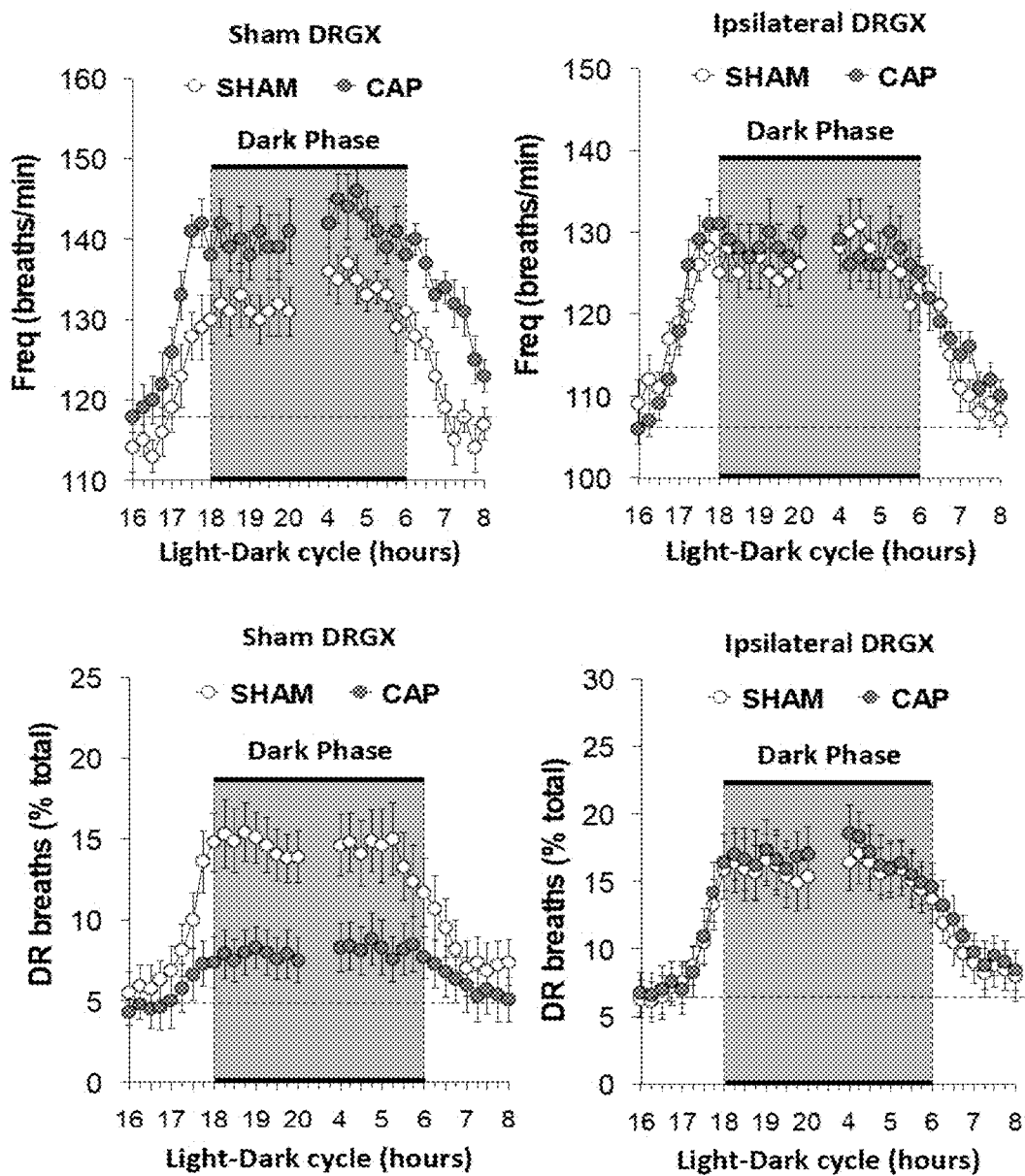

FIG. 6: Left renal artery Infusion of capsaicin diminishes disordered breathing (% total time) in freely-moving Sprague-Dawley rats. There were 9 rats in each group. The data are presented as mean±SEM.

Figure 7:
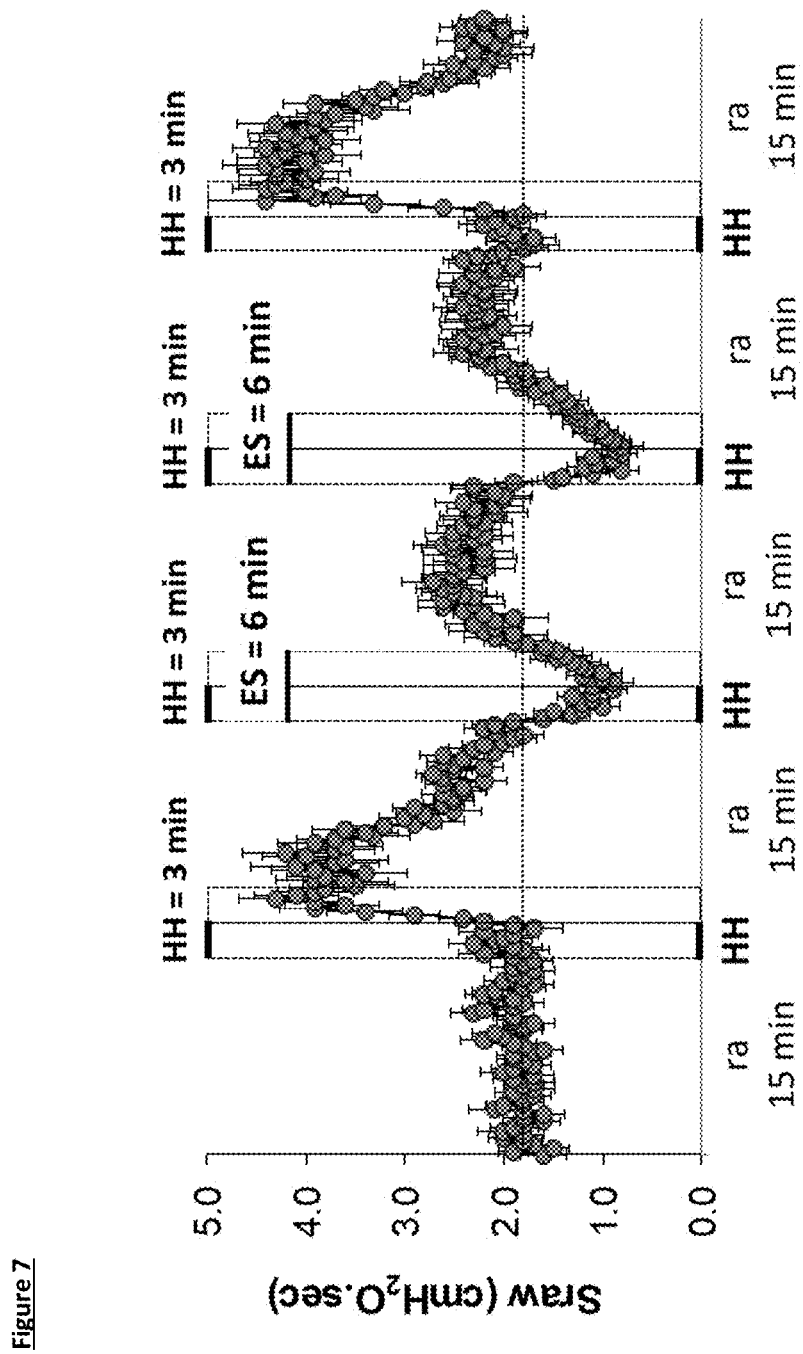

FIG. 7: Changes in airway resistance (Sraw, cmH2O.sec) elicited by electrical stimulation of renal nerves in freely-moving Zucker-fat rats. The data are the mean±SEM from 9 rats.

Figure 8:
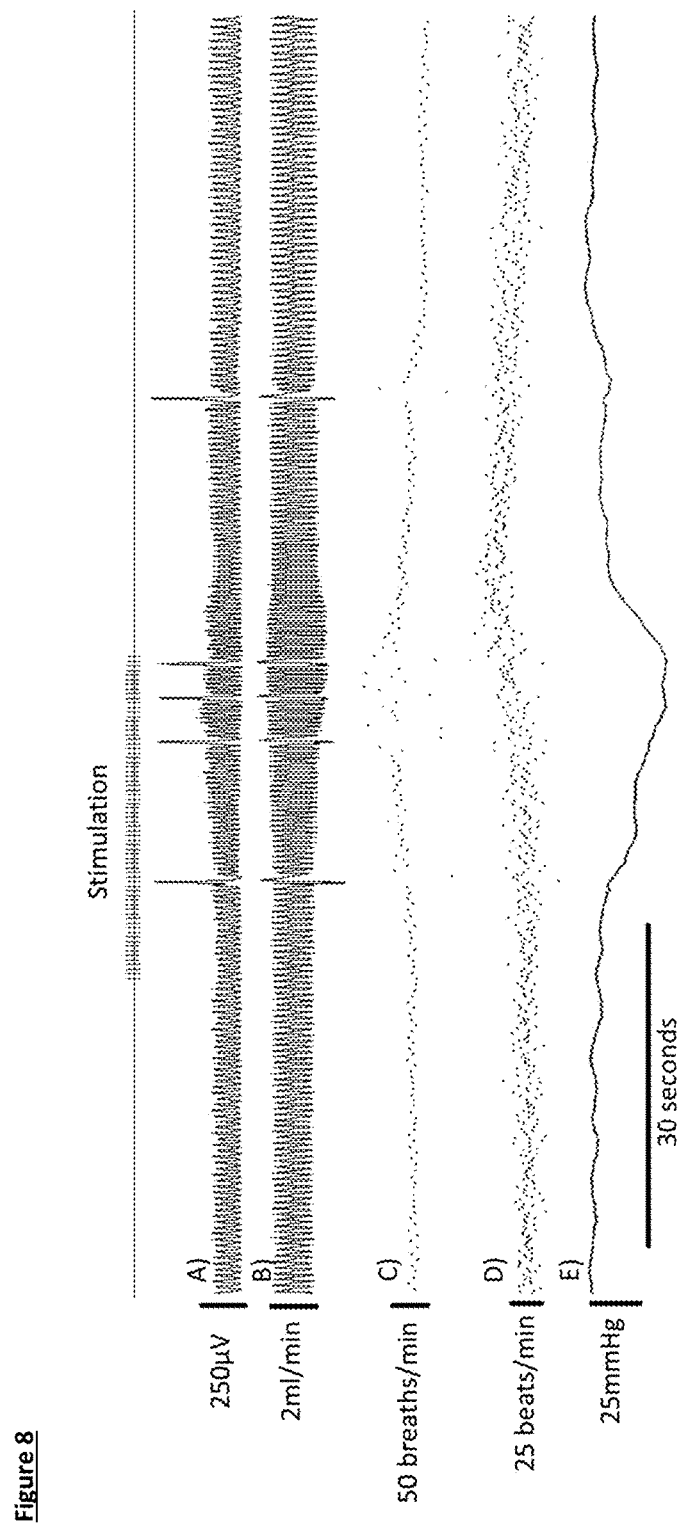

FIG. 8: A representative trace showing the effect of left renal afferent nerve stimulation on cardiorespiratory parameters in a sodium pentobarbitone anaesthetised male Zucker Fat rat. Diaphragmatic EMG (A), air flow (B), respiratory rate (C) and heart rate (D) were increased with renal afferent stimulation (2.5 Hz, 0.5 ms, 0.3 mA, 30 seconds), while blood pressure was decreased (E).

Figure 9:
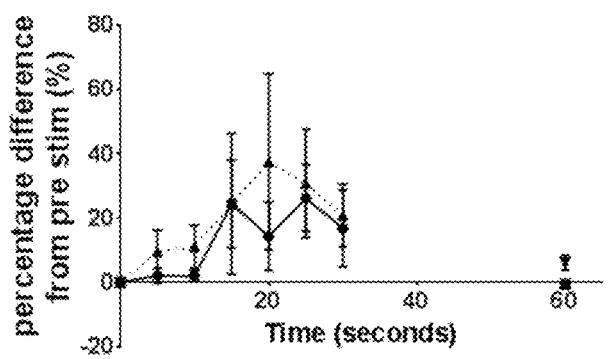
Figure 9:
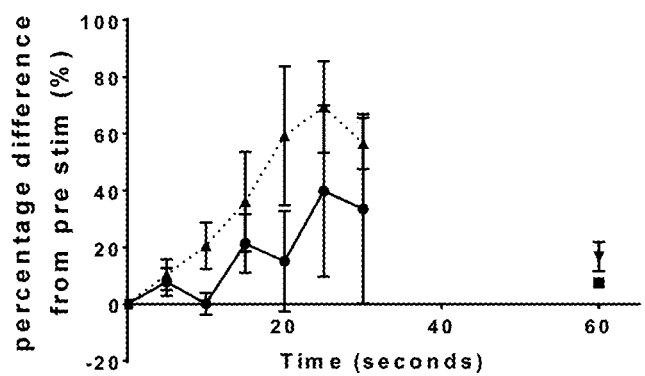
Figure 9:
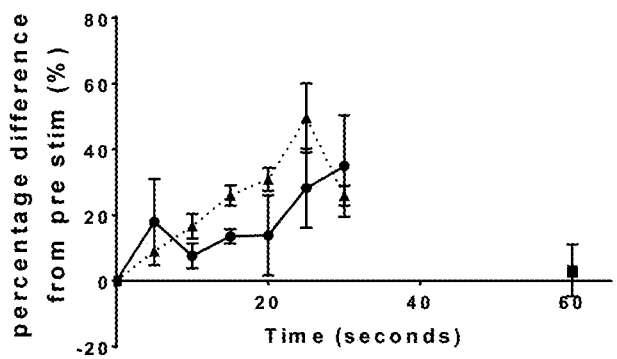
Figure 9:
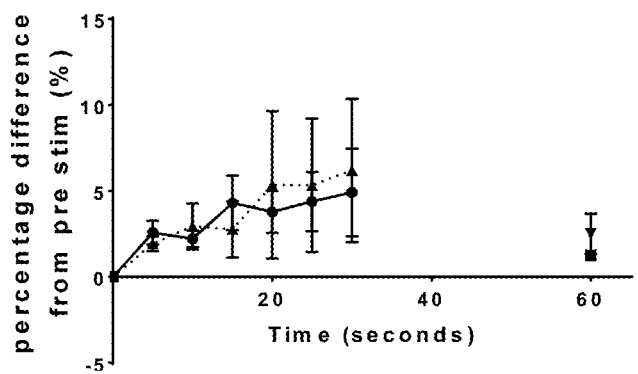
Figure 9:
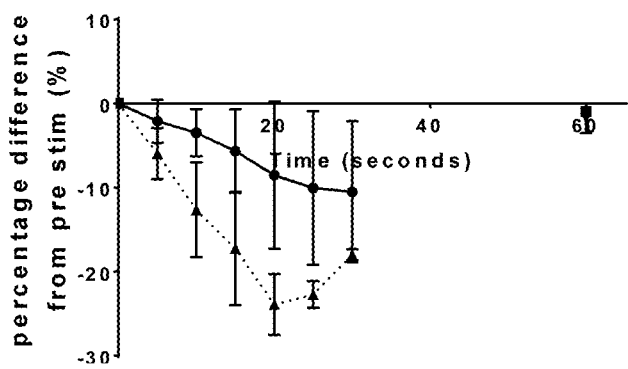

FIG. 9: Effect of left renal afferent nerve stimulation on cardiorespiratory parameters in sodium pentobarbitone anaesthetised male Zucker Fat rats. In male Zucker Fat rats stimulation (2.5 Hz, 0.5 ms, 0.5 mA, 30 seconds and 5 Hz, 0.5 ms, 0.5 mA, 30 seconds) of the left renal afferents with a bipolar electrode increases diaphragmatic EMG (A), air flow (B), respiration rate (C) and heart rate (D), while decreasing blood pressure (E) in frequency dependent manner. ●2.5 Hz, ▲5 Hz, ■ measurement 60 seconds post stimulation to show return to baseline. Horizontal bar denotes stimulation period of 30 seconds. Mean data±S.E.M of 3 animals.

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, "transducer" is taken to mean any element of applying a signal to the nerve, for example an electrode, diode, Peltier element or ultrasound transducer.

As used herein, "neural activity" of a nerve is taken to mean the signalling activity of the nerve, for example the amplitude, frequency and/or pattern of action potentials in the nerve.

Modulation of neural activity, as used herein, is taken to mean that the signalling activity of the nerve is altered from the baseline neural activity—that is, the signalling activity of the nerve in the patient prior to any intervention. Such modulation may increase, inhibit, block, or otherwise change the neural activity compared to baseline activity.

Stimulation of neural activity is an increase in neural activity. This may be an increase in the total signalling activity of the whole nerve, or that the total signalling activity of a subset of nerve fibres of the nerve is increased, compared to baseline neural activity in that part of the nerve.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation (e.g. stimulation) of neural activity may comprise altering the neural activity in other ways, for example increasing a particular part of the neural activity and/or stimulating new elements of activity, for example in particular intervals of time, in particular frequency bands, according to particular patterns and so forth.

Modulation (e.g. stimulation) of the neural activity may be temporary. As used herein, "temporary" is taken to mean that the modulated neural activity (e.g. stimulation) is not permanent. That is, the neural activity following cessation of the signal is substantially the same as the neural activity prior to the signal being applied—i.e. prior to modulation.

Modulation (e.g. stimulation) of the neural activity may be persistent. As used herein, "persistent" is taken to mean that the modulated neural activity (e.g. stimulation) has a prolonged effect. That is, upon cessation of the signal, neural activity in the nerve remains substantially the same as when the signal was being applied—i.e. the neural activity during and following modulation is substantially the same.

Modulation of the neural activity may be corrective. As used herein, "corrective" is taken to mean that the modulated neural activity (e.g. stimulation) alters the neural activity towards the pattern of neural activity in a healthy individual. That is, upon cessation of the signal, neural activity in the nerve more closely resembles the pattern of action potentials in the nerve observed in a healthy subject than prior to modulation, preferably substantially fully resembles the pattern of action potentials in the nerve observed in a healthy subject.

For example, application of the signal may result in stimulation of neural activity, and upon cessation of the signal, the pattern of action potentials in the nerve resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy individual.

As used herein, sleep apnoea (or sleep apnea) is used to refer to disorders characterised by interruptions in breathing during sleep and/or by shallow or infrequent breathing. "Sleep apnoea" as used herein encompasses central sleep apnoea (CSA) and obstructive sleep apnoea (OSA) unless specified otherwise. An "apnoeic episode" is taken to mean a single disordered breath or interruption in breathing. Risk factors for sleep apnoea include (but are not limited to) obesity, smoking, nasopharyngeal anatomical abnormalities, neck size greater than 16 inches.

As used herein, the neural activity in a renal nerve of a healthy individual is that neural activity exhibited by a patient who does not have sleep apnoea.

As used herein, an "improvement in a measurable physiological parameter" is taken to mean that for any given physiological parameter, an improvement is a change in the value of that parameter in the patient towards the normal value or normal range for that parameter—i.e. towards the expected value in a healthy individual.

For example, in a patient suffering from sleep apnoea, the measurable physiological parameter may be selected from: sympathetic tone, duration of apnoeic episodes, frequency of apnoeic episodes, blood pressure, heart rate, respiratory rate, tidal volume, upper airway resistance, blood oxygen level, blood $CO_2$ level, alveolar-arterial gradient (A-a gradient), disordered breathing index (DBI), and diaphragmatic muscle activity (also referred to as diaphragmatic tone). For example, in a subject suffering from sleep apnoea, an improvement in a measurable parameter may be: an increase in sympathetic tone, a decrease in duration of apnoeic episodes, a decrease in frequency of apnoeic episodes, a decrease in blood pressure (for example a decrease in mean arterial pressure), a decrease in respiratory rate, an increase in respiratory rate, a change in respiratory rate towards a level characteristic of a healthy subject, an increase in tidal volume, a decrease in upper airway resistance, an increase or decrease in blood oxygen level towards a level characteristic of a healthy individual, an increase or decrease in blood $CO_2$ level towards a level characteristic of a healthy individual, an increase or decrease in A-a gradient towards a level characteristic of a healthy individual, a decrease in DBI, an increase in diaphragmatic muscle activity.

As used herein, "disordered breathing index (DBI)" and "percentage of disrupted breaths" are used interchangeably to refer to the number of disrupted breaths (i.e. apnoeic episodes or sighs) as a percentage of total breaths. Disrupted breaths can be determined, for example, by monitoring the respiratory traces of a subject, as would be familiar to the skilled person.

The physiological parameter may comprise an action potential or pattern of action potentials in a nerve of the patient. An improvement in such a parameter is characterised by the action potential or pattern of action potentials in the nerve more closely resembling that exhibited by a healthy individual than before the intervention.

As used herein, a physiological parameter is not affected by modulation of the neural activity if the parameter does not change as a result of the modulation from the average value of that parameter exhibited by the subject or patient when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a patient when the value for that parameter exhibited by the patient at the time of detection is determined. A detector is any element able to make such a determination.

A "predefined threshold value" for a physiological parameter is the value for that parameter where that value or beyond must be exhibited by a subject or patient before the intervention is applied. For any given parameter, the threshold value may be a value indicative of predisposition to sleep apnoea, and/or an imminent or ongoing episode of apnoea. Examples of such predefined threshold values include sympathetic tone (as determined by neural, hemodynamic (e.g. heart rate, blood pressure, heart rate variability) or circulating plasma/urine biomarkers) greater than a threshold sympathetic tone, for example greater than sympathetic tone in a healthy individual; blood pressure higher than that characteristic of a healthy individual; a respiratory rate higher than that characteristic of a healthy individual; a respiratory rate lower than that characteristic of a healthy individual; a tidal volume lower than that characteristic of a healthy individual; an upper airway resistance higher than that characteristic of a healthy individual; a disrupted breathing index higher than that characteristic of a healthy individual; a blood oxygen concentration lower than that characteristic of a healthy individual; a blood $CO_2$ concentration higher than that characteristic of a healthy individual; an alveolar-arterial gradient (A-a gradient) higher than that characteristic of a healthy individual; an alveolar-arterial gradient (A-a gradient) lower than that characteristic of a healthy individual, a DBI higher than that characteristic of a healthy individual. Appropriate values for any given parameter would be simply determined by the skilled person.

Such a threshold value for a given physiological parameter is exceeded if the value exhibited by the patient is beyond the threshold value—that is, the exhibited value is a greater departure from the normal or healthy value for that parameter than the predefined threshold value.

Treatment of sleep apnoea as used herein, for example treatment of CSA or treatment of OSA, is characterised by the subject exhibiting less frequent and/or less severe episodes of sleep apnoea than before treatment. Treatment may be characterised by amelioration of an ongoing apnoeic episode. For example, treatment may be applied when the patient is undergoing an apnoeic episode and results in at least partial relief of the apnoeic episode, preferably full relief of the apnoeic episode (i.e. a return to healthy breathing pattern). Treatment may be indicated by one or more of: a decrease in duration of apnoeic episodes, a decrease in frequency of apnoeic episodes, an increase in respiratory drive, an increase in blood oxygen (decreased hypoxia), a decrease in blood $CO_2$ (decreased hypercapnia), a decrease in respiratory rate, an increase in tidal volume, a decrease in upper airway resistance, a decrease in disrupted breathing index.

A "neuromodulation device" or "neuromodulation apparatus" as used herein is a device configured to modulate, preferably stimulate, the neural activity of a nerve. "Device" and "apparatus" are used interchangeably herein. Neuromodulation devices as described herein comprise at least one transducer or actuator (the terms are used interchangeably) capable of effectively applying a signal to a nerve. In those embodiments in which the neuromodulation device is at least partially implanted in the patient, the elements of the device that are to be implanted in the patient are constructed such that they are suitable for such implantation. Such suitable constructions would be well known to the skilled person. Indeed, various fully implantable neuromodulation devices are currently available, such as the vagus nerve stimulator of SetPoint Medical, in clinical development for the treatment of rheumatoid arthritis (Arthritis & Rheumatism, Volume 64, No. 10 (Supplement), page 5195 (Abstract No. 451), October 2012. "Pilot Study of Stimulation of the Cholinergic Anti-Inflammatory Pathway with an Implantable Vagus Nerve Stimulation Device in Patients with Rheumatoid Arthritis", Frieda A. Koopman et al), and the INTERSTIM™ device (Medtronic, Inc), a fully implantable device utilised for sacral nerve modulation in the treatment of overactive bladder.

As used herein, "implanted" is taken to mean positioned at least partially within the patient's body. Partial implantation means that only part of the device is implanted—i.e. only part of the device is positioned within the patient's body, with other elements of the device external to the patient's body. Wholly implanted means that the entire of the device is positioned within the patient's body. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the patient's body.

As shown herein, it has been identified that sleep apnoea can be treated by stimulation of a renal nerve, preferably stimulation of afferent fibres of the renal nerve. This stimulation of the renal nerve reduces the disordered breathing events associated with sleep apnoea, decreases airway resistance and decreases the duration of apnoeic events.

A neuromodulation device that stimulates the neural activity in a renal nerve of a subject will therefore provide an effective treatment for sleep apnoea.

Therefore, in accordance with a first aspect of the invention there is provided an apparatus for stimulating neural activity in a renal nerve subject, the apparatus comprising: a transducer configured to apply a signal to the nerve; and a controller coupled to the transducer, the controller controlling the signal to be applied by the transducer, such that the signal increases the neural activity of the nerve to produce a physiological response in the patient.

In certain such embodiments, the signal applied by the one or more transducers is an electrical signal, an optical signal, an ultrasonic signal, or a thermal signal. In certain embodiments, each transducer may be comprised of one or more electrodes, one or more photon sources, one or more ultrasound transducers, one more sources of heat, or one or more other types of transducer arranged to put the signal into effect.

In certain embodiments, the signal applied is an electrical signal, for example a voltage or current, and the transducer is an electrode. In certain such embodiments the signal applied comprises a direct current (DC) waveform, such as a charge balanced direct current waveform, or an alternating current (AC) waveform, or both a DC and an AC waveform.

In certain embodiments, the DC waveform or AC waveform may be a square, sinusoidal, triangular, stepped, sawtooth (positive or negative sloping), or complex waveform. The DC waveform may alternatively be a constant amplitude waveform. In certain embodiments the electrical signal is a DC square waveform, optionally of varying voltage.

It will be appreciated by the skilled person that the current/voltage of an applied electrical signal necessary to achieve the intended voltage/current stimulation (respectively) will depend upon the positioning of the electrode and the associated electrophysiological characteristics (e.g. impedance).

It is within the ability of the skilled person to determine the appropriate current/voltage for achieving the intended stimulation in a given subject. For example, the skilled person is aware of methods suitable to monitor the neural activity profile induced by neuronal or nerve stimulation.

In certain embodiments, the electrical signal has a frequency of about 0.5-50 Hz, optionally of about 0.5-25 Hz, optionally about 1-10 Hz, optionally 1-5 Hz. In certain embodiments, the electrical signal has a frequency of about 2-25 Hz, about 2-10 Hz, about 2-5 Hz or about 2-2.5 Hz. In certain preferred embodiments, the electrical signal has a frequency in the range of about 1 Hz to about 10 Hz, more preferably from about 2 Hz to about 5 Hz. In certain preferred embodiments, the electrical signal has a frequency in the range of from about 5 Hz to about 10 Hz.

In certain embodiments, the signal is an electrical signal having a frequency of at least about 2 Hz, optionally at least about 2.5 Hz. In certain embodiments, the electrical signal has a frequency of at least 5 Hz.

In certain embodiments, the signal is an electrical signal having a frequency of about 2 Hz, or about 2.5 Hz. In certain alternative embodiments, the electrical signal has a frequency of about 5 Hz.

In certain embodiments, the signal is an electrical signal having a voltage of about 1-20V. In certain preferred embodiments, the signal has a voltage of about 5-15V, optionally about 10-15V. In certain embodiments, the signal is an electrical signal having a voltage of at least about 14V. In certain preferred embodiments the voltage is about 14V.

In certain embodiments, the signal is an electrical signal having a current of about 0.01-2 mA, optionally about 0.05-1 mA, optionally about 0.075-0.5 mA, optionally 0.1-0.5 mA. In certain embodiments, the signal has a current in the range of from about 0.08-0.15 mA.

In certain embodiments, the signal is an electrical signal having a current of at least about 0.01 mA, at least about 0.02 mA, at least about 0.03 mA, at least about 0.04 mA, at least about 0.05 mA, at least about 0.06 mA, at least about 0.07 mA, at least about 0.08 mA, at least about 0.09 mA, at least about 0.1 mA. In certain embodiments, the signal has a current of at least about 0.3 mA, for example at least about 0.5 mA.

In certain embodiments, the signal is an electrical signal having a current of about 0.1 mA. In certain embodiments, the signal is an electrical signal having a current of about 0.3 mA. In certain embodiments, the signal is an electrical signal having a current of about 0.5 mA.

In certain embodiments the signal is an electrical signal having a pulse width of about 0.1-5 ms, optionally about 0.1-2 ms, optionally about 0.2-1 ms, optionally about 0.25-0.75 ms, optionally 0.5 ms. In certain embodiments the signal is an electrical signal and the signal has a pulse duration of less than or equal to about 1 ms, optionally less than or equal to about 0.9 ms, optionally less than or equal to about 0.8 ms, optionally less than or equal to about 0.7 ms, optionally less than or equal to about 0.6 ms, optionally less than or equal to about 0.5 ms. In certain embodiments, the signal has a pulse width of about 0.5 ms.

In certain preferred embodiments, the signal comprises a DC waveform, optionally a square waveform, of about 0.1 mA, 0.3 mA or 0.5 mA, and about 0.5 ms pulse width, with a frequency of at least about 2 Hz, at least about 2.5 Hz. In certain embodiments, the signal has a frequency of from about 2 Hz to about 5 Hz, optionally from about 2 Hz to about 2.5 Hz. In certain such embodiments, the signal has a frequency of about 2 Hz, about 2.5 Hz, or about 5 Hz.

In those embodiments in which the signal applied is an electrical signal and the transducer configured to apply the electrical signal is an electrode, the electrode may be a cuff or wire electrode. In certain embodiments the electrode is bipolar or tripolar.

In certain embodiments wherein the signal applied by the transducer is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the transducer is a thermal signal, the transducer configured to apply a thermal signal.

In certain embodiments, the transducer comprises a Peltier element configured to apply a thermal signal. In certain embodiments, the transducer comprises a laser diode configured to apply a thermal signal. In certain embodiments, the transistor comprises an electrically resistive element configured to apply a thermal signal.

In certain embodiments the signal applied by the transducer is a mechanical signal, optionally an ultrasonic signal. In certain alternative embodiments, the mechanical signal applied by the transducer is a pressure signal.

In certain embodiments the signal applied by the transducer is an electromagnetic signal, optionally an optical signal. In certain such embodiments, the transducer comprises a laser and/or a light emitting diode configured to apply the optical signal.

In certain embodiments, the neuromodulation apparatus comprises additional transducers configured to apply a signal, for example an additional 1, 2, 3, 4 or 5 transducers. In certain preferred embodiments, the apparatus comprises 2 transducers each configured to apply a signal to a renal nerve of a subject. In certain such embodiments, the transducers are capable of being positioned for bilateral stimulation of the renal nerves.

In embodiments in which the apparatus comprises a plurality of transducers, the embodiments of the signal described herein apply equally and independently to each of the transducers. That is, in certain embodiments, each transducer applies a different signal to the other transducers. In certain alternative embodiments, each transducer is configured to apply the same signal.

In certain embodiments, the physiological response produced in the patient is an improvement in one or more a measurable physiological parameter selected from: sympathetic tone, duration of apnoeic episodes, frequency of apnoeic episodes, blood pressure, respiratory rate, tidal volume, upper airway resistance, blood oxygen levels, blood $CO_2$ levels, alveolar-arterial gradient (A-a gradient), disrupted breathing index (DBI), and diaphragmatic muscle activity. For example, the physiological response may be one or more of: a decrease in duration of apnoeic episodes, a decrease in frequency of apnoeic episodes, an increase in respiratory drive, an increase in blood oxygen (decreased hypoxia), a decrease in blood $CO_2$ (decreased hypercapnia), a decrease in respiratory rate, an increase in respiratory rate, a change in respiratory rate towards a level characteristic of a healthy subject, an increase in tidal volume, a decrease in upper airway resistance, a decrease in DBI, a change in A-a gradient towards an A-a gradient characteristic of a healthy individual, an increase in diaphragmatic EMG activity.

In certain embodiments, the apparatus further comprises a detector element to detect one or more physiological parameters in the patient. In certain embodiments, the one or more detected physiological parameters are selected from sympathetic tone, duration of apnoeic episodes, frequency of apnoeic episodes, blood pressure, respiratory rate, tidal volume, upper airway resistance, blood oxygen level, blood $CO_2$ level, alveolar-arterial gradient (A-a gradient), disordered breathing index (DBI), and diaphragmatic muscle activity. In certain embodiments, the one or more detected physiological parameters comprise an action potential or pattern of action potentials in a nerve of the patient, wherein the action potential or pattern of action potentials is associated with sleep apnoea. In certain such embodiments, the nerve is the renal nerve.

The detector element may be configured to detect one or more physiological parameters. That is, in such embodiments each detector may detect more than one physiological parameter, for example all the detected physiological parameters. Alternatively, the apparatus may comprise one or more detectors each configured to detect a separate parameter of the one or more physiological parameters detected.

In such embodiments, the controller is coupled to the detector element configured to detect one or more physiological parameters, and causes the transducer or transducers to apply the signal when the physiological parameter is detected to be meeting or exceeding a predefined threshold value.

It will be appreciated that any two or more of the indicated physiological parameters may be detected in parallel or consecutively. For example, in certain embodiments, the controller is coupled to a detector or detectors configured to detect the pattern of action potentials in a renal nerve and also to detect the blood pressure of the patient.

Application of the signal by an apparatus according to the invention causes an increase in neural activity in the nerve or nerves to which the signal is applied. That is, application of the signal results in the neural activity in at least part of the nerve or nerves being increased compared to the baseline neural activity in that part of the nerve.

In certain embodiments, the signal increases neural activity in afferent fibres of the nerve (for example afferent C fibres). That is, in such embodiments, application of the signal to the nerve results in an increase in neural activity in at least afferent fibres of the nerve, for example in afferent C fibres. In certain embodiments, the signal increases neural activity across the whole nerve.

In certain embodiments, the signal selectively increases neural activity in afferent fibres of the nerve. That is, the signal preferentially increases activity in afferent fibres of the renal nerve compared to the level of activity induced in other fibres. In certain embodiments, the signal increases neural activity only in afferent fibres of the renal nerve.

In certain embodiments, the signal selectively increases neural activity in afferent C fibres of the nerve. That is, the signal preferentially increases activity in afferent C fibres of the renal nerve compared to the level of activity induced in other fibres. In certain embodiments, the signal increases neural activity only in afferent C fibres of the renal nerve.

Selective stimulation of a subset of fibres can be achieved, for example, using particular pulse shapes or waveforms. For example, a stepped waveform including a sub-threshold depolarizing step selectively stimulates small diameter fibres (e.g. C fibres) (Vuckovic et al 9th Annual Conference of the International FES Society September 2004, which is incorporated herein by reference). By way of further example, saw-tooth waveforms (either with exponentially positive slope or with exponentially negative slope) are able to selectively stimulate subsets of fibres. In particular, exponentially positive slope waveforms selectively stimulate small diameter fibres (e.g. C fibres) (Vuckovic et al, ibid), and exponentially negative slope waveforms selectively stimulate unmyelinated fibres (i.e. C fibres) (Accornero et al, J. Physiol. (1977), 273, pp. 539-560, incorporated herein by reference).

In certain embodiments, neural activity may be further modulated as a result of applying the signal, for example resulting in an alteration to the pattern of action potentials in the nerve or nerves. In certain such embodiments, the neural activity is modulated such that the resultant pattern of action potentials in the nerve or nerves resembles the pattern of action potentials in the nerve or nerves observed in a healthy subject. Such modulation may comprise altering the neural activity in various other ways, for example increasing or inhibiting a particular part of the activity and stimulating new elements of activity, for example in particular intervals of time, in particular frequency bands, according to particular patterns and so forth.

In certain embodiments, the controller causes the signal to be applied intermittently. In certain such embodiments, the controller causes the signal to applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is independently selected from any time from about 5 seconds (5 s) to about 24 hours (24 h), about 30 s to about 12 h, about 1 min to about 12 h, about 5 min to about 8 h, about 5 min to about 6 h, about 10 min to about 6 h, about 10 min to about 4 h, about 30 min to about 4 h, about 1 h to about 4 h. In certain embodiments, the duration of each of the first, second, third and fourth time periods is independently selected from 5 s, 10 s, 15 s, 30 s, 45 s, 60 s, 2 min, 5 min, 6 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments the signal is applied for at least about 10 s, for example at least about 15, 20, 25 or 30 s. In certain embodiments, the signal is applied for at least about 30 s with a rest period of at least about 30 s. In certain embodiments, the signal is applied for at least about 45 s with a rest period of at least about 15 s. In certain embodiments, the signal is applied for at least for at least about 5 min with a rest period of at least about 5 min. In certain embodiments the rest period between signals is at least about 15 minutes.

In certain embodiments wherein the controller causes the signal to be applied intermittently, the signal is applied for a specific amount of time per day. In certain such embodiments, the signal is applied for about 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified duration.

In certain embodiments wherein the controller causes the signal to be applied intermittently, the signal is applied only when the subject is in a specific physiological state. For example, in certain embodiments, the signal may be applied only when the subject is asleep, and/or only when the subject is undergoing an apnoeic episode.

In certain such embodiments, the apparatus further comprises a communication, or input, element via which the status of the patient (e.g. that they are going to sleep) can be indicated by the patient or a physician. In alternative embodiments, the apparatus further comprises a detector configured to detect the status of the patient, wherein the signal is applied only when the detector detects that the patient is in the specific state. As described above, in certain embodiments, the detector detects that the subject is undergoing an apnoeic episode characterised by one or more physiological parameters being at or beyond the threshold value for each parameter. In response, the controller causes a signal to be applied.

In certain alternative embodiments, the controller causes the signal to be permanently applied. That is, once begun, the signal is continuously applied to the nerve. It will be appreciated that in embodiments wherein the signal is a series of pulses, gaps between pulses do not mean the signal is not continuously applied.

In certain embodiments of the apparatus, the increase in neural activity caused by the application of the signal is temporary. That is, upon cessation of the signal, neural activity in the nerve returns substantially towards baseline neural activity within about 1-60 seconds, or within about 1-60 minutes, for example within about 5 minutes, or within about 1-24 hours, optionally about 1-12 hours, optionally about 1-6 hours, optionally about 1-4 hours, optionally about 1-2 hours. In certain such embodiments, the neural activity returns substantially fully to baseline neural activity. That is, the neural activity following cessation of the signal is substantially the same as the neural activity prior to the signal being applied—i.e. prior to stimulation. In certain alternative embodiments, the neural activity returns to a baseline neural activity that may be different from the neural activity prior to stimulation.

As demonstrated herein, the renal nerve can be stimulated such that the physiological effect of stimulation is temporary. That is, the change in one or more physiological parameters such as respiration rate, diaphragmatic contraction, tidal volume and blood pressure induced by renal nerve stimulation is exhibited only during and shortly after stimulation. In such embodiments, upon cessation of stimulation, the one or more physiological parameters change to a level different to the level exhibited during stimulation. In certain preferred embodiments, the one or more physiological parameters return to baseline (i.e. pre-stimulation) levels upon cessation of stimulation. This may be advantageous, for example, when treating conditions with transient or intermittent symptoms. For instance, application of the stimulation during an acute apnoeic episode can treat the condition without the effects of stimulation impacting on normal respiration. Therefore, in certain embodiments, the effect on a physiological parameter of renal nerve stimulation is temporary. In certain such embodiments, the physiological parameter returns to baseline level within 10 minutes, optionally within 5 minutes of signal cessation, optionally within 2 minutes, optionally within about 60 s of signal cessation.

In certain alternative embodiments, the increase in neural activity caused by the application of the signal or signals is substantially persistent. That is, upon cessation of the signal, neural activity in the nerve or nerves remains substantially the same as when the signal was being applied—i.e. the neural activity during and following stimulation is substantially the same.

In certain embodiments, the increase in neural activity caused by the application of the signal is partially corrective, preferably substantially corrective. That is, upon cessation of the signal, neural activity in the nerve more closely resembles the pattern of action potentials in the nerve observed in a healthy subject than prior to stimulation, preferably substantially fully resembles the pattern of action potentials in the nerve observed in a healthy subject. For example, application of the signal may result in an increase in neural activity, and upon cessation of the signal, the pattern of action potentials in the nerve resembles the pattern of action potentials observed in a healthy individual. It is hypothesised that such a corrective effect is the result of a positive feedback loop—that is, the underlying predisposition to sleep apnoea is treated as result of the stimulation caused by application of the signal.

In certain embodiments, the apparatus is suitable for at least partial implantation into the patient. In certain such embodiments, the apparatus is suitable to be fully implanted in the patient.

In certain embodiments, the apparatus further comprises one or more power supply elements, for example a battery, and/or one or more communication elements.

In a second aspect, the invention provides a method of treating sleep apnoea (OSA and/or CSA), the method comprising implanting an apparatus according to the first aspect, positioning the transducer of the apparatus in signalling contact with a renal nerve of a patient, and activating the apparatus. In such embodiments, the transducer is in signalling contact with the nerve when it is positioned such that the signal can be effectively applied to the nerve. The apparatus is activated when the apparatus is in an operating state such that the signal will be applied as determined by the controller.

Implementation of all aspects of the invention (as discussed both above and below) will be further appreciated by reference to FIGS. 2A-2C.

Figure 2A:
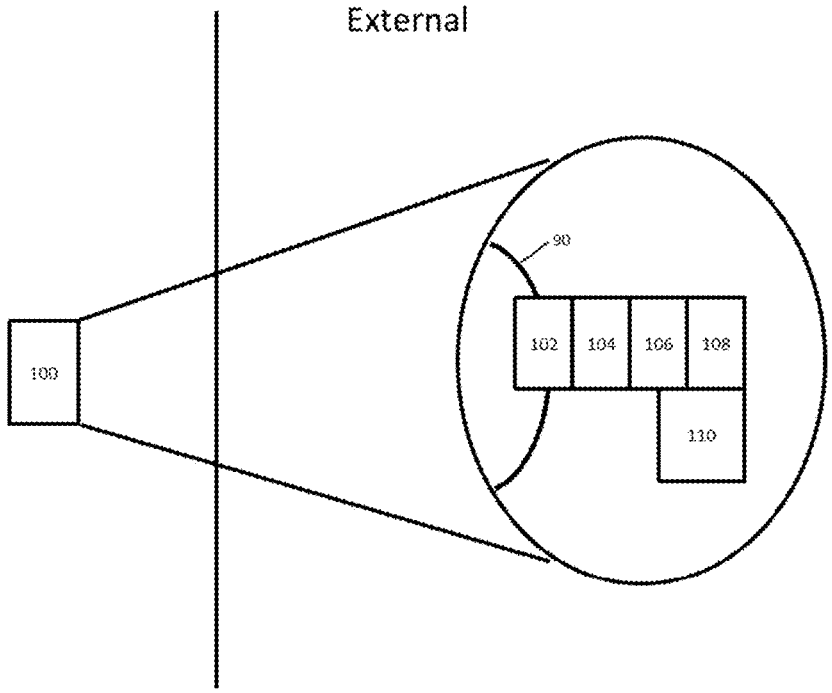
Figure 2B:
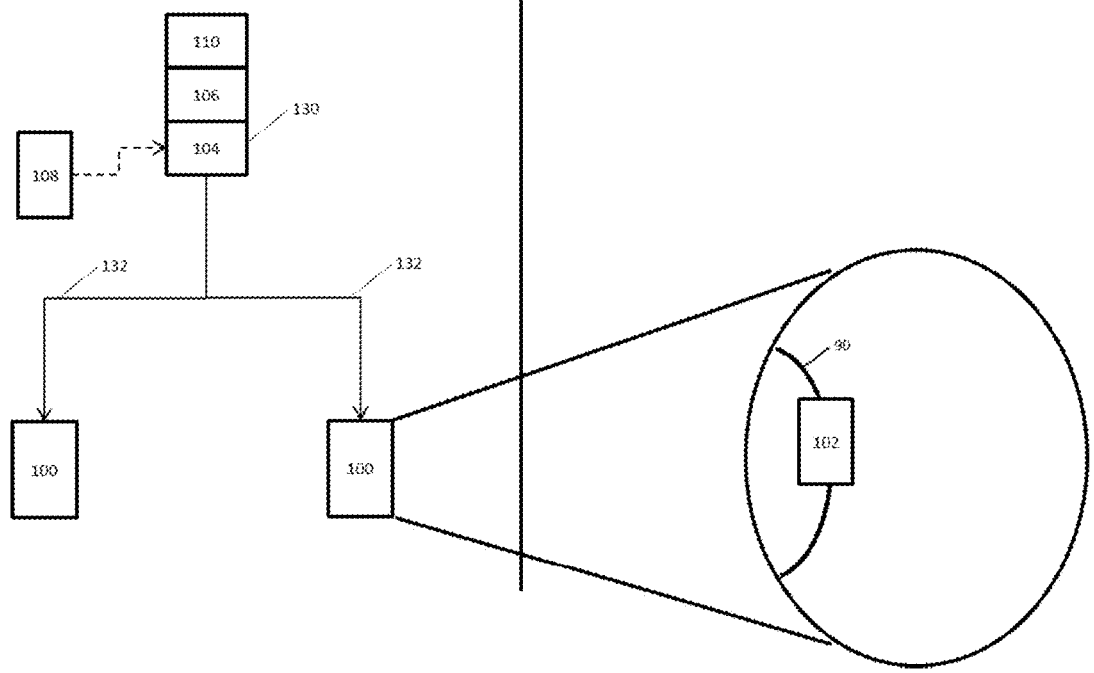
Figure 2C:
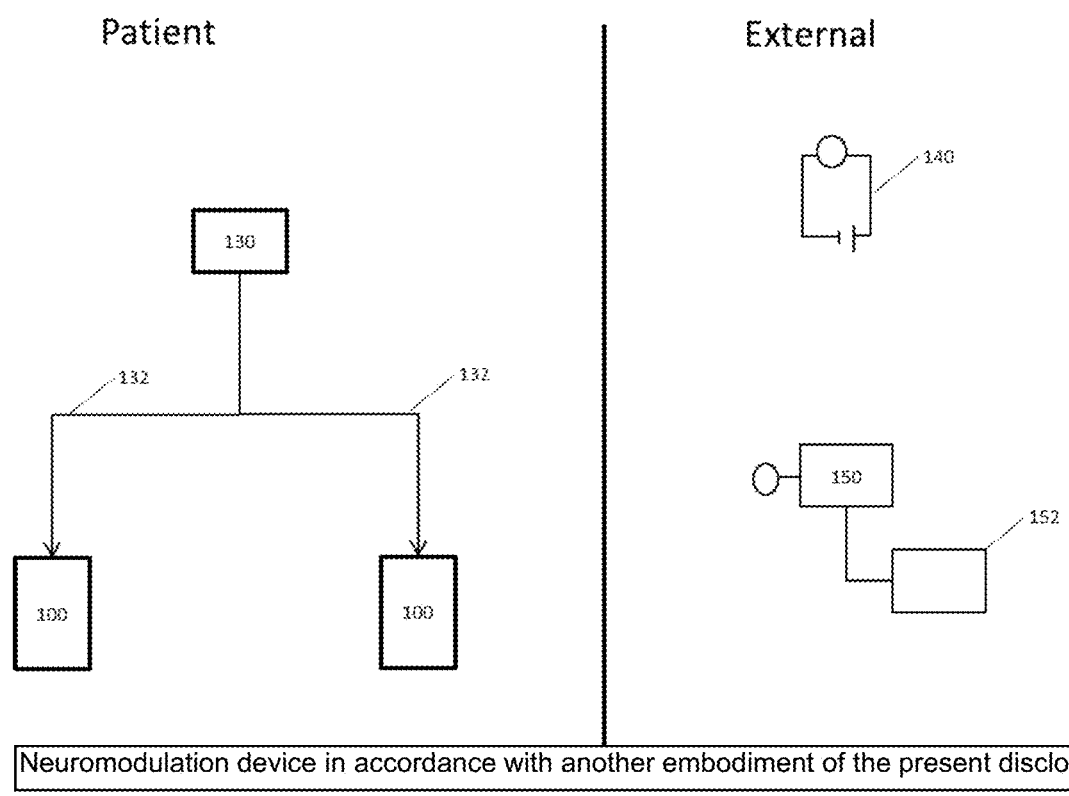

FIGS. 2A-2C show how the invention may be put into effect using one or more neuromodulation devices which are implanted in, located on, or otherwise disposed with respect to a patient in order to carry out any of the various methods described herein. In this way, one or more neuromodulation apparatuses can be used to treat sleep apnoea in a patient, by stimulating neural activity in a renal nerve of the patient.

In each of the FIGS. 2B-2C a separate neuromodulation device 100 is provided in respect of each of the left and right renal nerve, although as discussed herein a device could be provided or used in respect of only one of the renal nerves. Each such neuromodulation device may be fully or partially implanted in the patient, or otherwise located, so as to provide neuromodulation of the respective nerve or nerves. Each of the left and right neuromodulation devices 100 may operate independently, or may operate in communication with each other.

FIG. 2A also shows schematically components of an implanted neuromodulation device 100, in which the device comprises several elements, components or functions grouped together in a single unit and implanted in the patient. A first such element is a transducer 102 which is shown in proximity to a renal nerve 90 of the patient. The transducer 102 may be operated by a controller element 104. The device may comprise one or more further elements such as a communication element 106, a detector element 108, a power supply element 110 and so forth.

Each neuromodulation device 100 may carry out the required neuromodulation independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological parameters, as described below.

FIG. 2B illustrates some ways in which the apparatus of FIG. 2A may be differently distributed. For example, in FIG. 2B the neuromodulation devices 100 comprise transducers 102 implanted proximally to a renal nerve 90, but other elements such as a controller 104, a communication element 106 and a power supply 110 are implemented in a separate control unit 130 which may also be implanted in, or carried by the patient. The control unit 130 then controls the transducers in both of the neuromodulation devices via connections 132 which may for example comprise electrical wires and/or optical fibres for delivering signals and/or power to the transducers.

In the arrangement of FIG. 2B one or more detectors 108 are located separately from the control unit, although one or more such detectors could also or instead be located within the control unit 130 and/or in one or both of the neuromodulation devices 100. The detectors may be used to detect one or more physiological parameters of the patient, and the controller element or control unit then causes the transducers to apply the signal in response to the detected parameter(s), for example only when a detected physiological parameter meets or exceeds a predefined threshold value.

Physiological parameters which could be detected for such purposes include sympathetic tone, duration of apnoeic episodes, frequency of apnoeic episodes, blood pressure, heart rate, respiratory rate, tidal volume, upper airway resistance, blood oxygen level, blood $CO_2$ level, alveolar-arterial gradient (A-a gradient), disordered breathing index (DBI), and diaphragmatic muscle activity. Similarly, a detected physiological parameter could be an action potential or pattern of action potentials in a nerve of the patient, for example a renal nerve, wherein the action potential or pattern of action potentials is associated with sleep apnoea.

A variety of other ways in which the various functional elements could be located and grouped into the neuromodulation devices, a control unit 130 and elsewhere are of course possible. For example, one or more sensors of FIG. 2B could be used in the arrangement of FIG. 2A or 2C or other arrangements.

FIG. 2C illustrates some ways in which some functionality of the apparatus of FIG. 2A or 2B is provided not implanted in the patient. For example, in FIG. 2C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input facility 152. The data input facility could be used by a patient or other operator in various ways, for example to input data relating to the status of the patient (e.g. if they are about to go to sleep).

Each neuromodulation device may be adapted to carry out the neuromodulation required using one or more physical modes of operation which typically involve applying a signal to a renal nerve, such a signal typically involving a transfer of energy to (or from) the nerve(s). As already discussed, such modes may comprise stimulating neural activity in the nerve using an electrical signal, an optical signal, an ultrasound or other mechanical signal, a thermal signal, a magnetic or electromagnetic signal, or some other use of energy to carry out the required stimulation. To this end, the transducer 102 illustrated in FIG. 2A could be comprised of one or more electrodes, one or more photon sources, one or more ultrasound transducers, one or more sources of heat, or one or more other types of transducer arranged to put the required neuromodulation into effect.

In certain embodiments, the signal applied is an electrical signal, for example a voltage or current, and the transducer is an electrode. In certain such embodiments the signal applied comprises a direct current (DC) waveform, such as a charge balanced direct current waveform, or an alternating current (AC) waveform, or both a DC and an AC waveform.

In certain embodiments, the DC waveform or AC waveform may be a square, sinusoidal, triangular, stepped, sawtooth, or complex waveform. The DC waveform may alternatively be a constant amplitude waveform. In certain embodiments the electrical signal is a DC square waveform, optionally of varying voltage.

It will be appreciated by the skilled person that the current/voltage of an applied electrical signal necessary to achieve the intended voltage/current stimulation (respectively) will depend upon the positioning of the electrode and the associated electrophysiological characteristics (e.g. impedance). It is within the ability of the skilled person to determine the appropriate current/voltage for achieving the intended stimulation in a given subject. For example, the skilled person is aware of methods suitable to monitor the neural activity profile induced by neuronal or nerve stimulation.

In certain embodiments, the electrical signal has a frequency of about 0.5-50 Hz, optionally of about 0.5-25 Hz, optionally about 1-10 Hz, optionally about 1-5 Hz. In certain embodiments, the electrical signal has a frequency of about 2-25 Hz, about 2-10 Hz, about 2-5 Hz or about 2-2.5 Hz. In certain preferred embodiments, the electrical signal has a frequency in the range of about 1 Hz to about 10 Hz, more preferably from about 2 Hz to about 5 Hz. In certain preferred embodiments, the electrical signal has a frequency in the range of from about 5 Hz to about 10 Hz.

In certain embodiments, the signal is an electrical signal having a frequency of at least about 2 Hz, optionally at least about 2.5 Hz. In certain embodiments, the signal has a frequency of at least about 5 Hz.

In certain embodiments, the signal is an electrical signal having a frequency of about 2 Hz, about 2.5 Hz, or about 5 Hz.

In certain embodiments, the signal is an electrical signal having a voltage of about 1-20V. In certain preferred embodiments, the signal has a voltage of about 5-15V, optionally about 10-15V. In certain embodiments, the signal is an electrical signal having a voltage of at least about 14V. In certain preferred embodiments the voltage is about 14V.

In certain embodiments, the signal is an electrical signal having a current of about 0.01-2 mA, optionally about 0.05-1 mA, optionally about 0.075-0.5 mA, optionally 0.1-0.5 mA. In certain embodiments, the signal has a current in the range of from about 0.08-0.15 mA.

In certain embodiments, the signal is an electrical signal having a current of at least about 0.01 mA, at least about 0.02 mA, at least about 0.03 mA, at least about 0.04 mA, at least about 0.05 mA, at least about 0.06 mA, at least about 0.07 mA, at least about 0.08 mA, at least about 0.09 mA, at least about 0.1 mA. In certain embodiments, the signal has a current of at least about 0.3 mA, optionally at least about 0.5 mA.

In certain embodiments, the signal is an electrical signal having a current of about 0.1 mA. In certain embodiments, the signal is an electrical signal having a current of about 0.3 mA. In certain embodiments, the signal is an electrical signal having a current of about 0.5 mA.

In certain embodiments the signal is an electrical signal having a pulse width of about 0.1-5 ms, optionally about 0.1-2 ms, optionally about 0.2-1 ms, optionally about 0.5 ms. In certain embodiments the signal is an electrical signal and the signal has a pulse duration of less than or equal to about 1 ms, optionally less than or equal to about 0.9 ms, optionally less than or equal to about 0.8 ms, optionally less than or equal to about 0.7 ms, optionally less than or equal to about 0.6 ms, optionally less than or equal to about 0.5 ms. In certain embodiments, the signal has a pulse width of about 0.5 ms.

In certain preferred embodiments, the signal comprises a DC waveform, optionally a square waveform, of about 0.1 mA, 0.3 mA or 0.5 mA, and about 0.5 ms pulse width, with a frequency of at least about 2 Hz, at least about 2.5 Hz. In certain embodiments, the signal has a frequency of from about 2 Hz to about 5 Hz, optionally from about 2 Hz to about 2.5 Hz. In certain such embodiments, the signal has a frequency of about 2 Hz, about 2.5 Hz, or about 5 Hz.

In those embodiments in which the signal applied is an electrical signal and the transducer configured to apply the electrical signal is an electrode, the electrode may be a cuff or wire electrode. In certain embodiments, the electrode is bipolar or tripolar.

It will be appreciated that in those embodiments in which more than one signal is applied (e.g. to different nerves by one device 100 or by multiple devices 100 each applying one signal), each signal is independently selected from the signal embodiments described above. In certain embodiments, each signal applied is the same as all other signals applied.

In a third aspect, the invention provides a method of treating sleep apnoea in a patient, for example OSA and/or CSA, the method comprising applying a signal to a renal nerve of said patient to increase neural activity in said nerve in the patient.

In certain embodiments, the signal is applied by a neuromodulation apparatus comprising one or more transducers configured to apply the signal. In certain preferred embodiments the neuromodulation apparatus is at least partially implanted in the patient. In certain preferred embodiments, the neuromodulation device is wholly implanted in the patient.

In certain embodiments, the treatment of sleep apnoea is treatment of CSA and/or treatment of OSA. In certain embodiments, the treatment is characterised by the subject exhibiting less frequent and/or less severe episodes of sleep apnoea than before treatment. In certain embodiments, treatment may be characterised by at least partial amelioration of an ongoing apnoeic episode, preferably complete amelioration of an ongoing apnoeic episode.

In certain embodiments, treatment of sleep apnoea is indicated by an improvement in a measurable physiological parameter, for example one or more physiological parameters selected from: sympathetic tone, duration of apnoeic episodes, frequency of apnoeic episodes, blood pressure, heart rate, respiratory rate, tidal volume, upper airway resistance, blood oxygen level, blood $CO_2$ level, alveolar-arterial gradient (A-a gradient), disordered breathing index (DBI), and diaphragmatic muscle activity. Suitable methods for determining the value for any given parameter would be appreciated by the skilled person.

It will be appreciated that treatment of sleep apnoea, for example OSA or CSA, may include improvement in one or more or all of the above characteristics. That is, treatment of sleep apnoea according to the method may be characterised by reduced upper airway resistance, and less frequent apnoeic episodes, with any episode also being less severe than before treatment.

In certain embodiments, treatment of the condition is indicated by an improvement in the profile of neural activity in the nerve to which the signal is applied. That is, treatment of the condition is indicated by the neural activity in the nerve approaching the neural activity in a healthy individual—i.e. the pattern of action potentials in the nerve more closely resembling that exhibited by a healthy individual than before the intervention.

Application of the signal by an apparatus according to the invention causes an increase in neural activity in the nerve or nerves to which the signal is applied. That is, application of the signal results in the neural activity in at least part of the nerve being increased compared to the baseline neural activity in that part of the nerve.

In certain embodiments, the signal increases neural activity in afferent fibres of the nerve (for example afferent C fibres). That is, in such embodiments, application of the signal to the nerve results in an increase in neural activity in at least afferent fibres of the nerve, for example in afferent C fibres. In certain embodiments, the signal increases neural activity across the whole nerve.

In certain embodiments, the signal selectively increases neural activity in afferent fibres of the nerve. That is, the signal preferentially increases activity in afferent fibres of the renal nerve compared to the level of activity induced in other fibres. In certain embodiments, the signal increases neural activity only in afferent fibres of the renal nerve.

In certain embodiments, the signal selectively increases neural activity in afferent C fibres of the nerve. That is, the signal preferentially increases activity in afferent C fibres of the renal nerve compared to the level of activity induced in other fibres. In certain embodiments, the signal increases neural activity only in afferent C fibres of the renal nerve.

Selective stimulation of a subset of fibres can be achieved, for example, using particular pulse shapes or waveforms. For example, a stepped waveform including a sub-threshold depolarizing step selectively stimulates small diameter fibres (e.g. C fibres) (Vuckovic et al 9th Annual Conference of the Vuckovic FES Society September 2004, which is incorporated herein by reference). By way of further example, saw-tooth waveforms (either with exponentially positive slope or with exponentially negative slope) are able to selectively stimulate subsets of fibres. In particular, exponentially positive slope waveforms selectively stimulate small diameter fibres (e.g. C fibres) (Vuckovic et al, ibid), and exponentially negative slope waveforms selectively stimulate unmyelinated fibres (i.e. C fibres) (Accornero et al, J. Physiol. (1977), 273, pp. 539-560, incorporated herein by reference).

Neural activity may also be modulated as a result of applying the signal such that there is an alteration to the pattern of action potentials in the nerve to which the signal is applied. In certain such embodiments, the neural activity is modulated such that the resultant pattern of action potentials in the nerve resembles the pattern of action potentials in the nerve observed in a healthy subject.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is independently selected from any time from about 5 seconds (5 s) to about 24 hours (24 h), about 30 s to about 12 h, about 1 min to about 12 h, about 5 min to about 8 h, about 5 min to about 6 h, about 10 min to about 6 h, about 10 min to about 4 h, about 30 min to about 4 h, about 1 h to about 4 h. In certain embodiments, the duration of each of the first, second, third and fourth time periods is independently selected from 5 s, 10 s, 15 s, 30 s, 45 s, 60 s, 2 min, 5 min, 6 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments the signal is applied for at least about 10 s, for example at least about 15, 20, 25 or 30 s. In certain embodiments, the signal is applied for at least about 30 s with a rest period of at least about 30 s. In certain embodiments, the signal is applied for at least about 45 s with a rest period of at least about 15 s. In certain embodiments, the signal is applied for at least for at least about 5 min with a rest period of at least about 5 min. In certain embodiments the rest period between signals is at least about 15 minutes.

In certain embodiments wherein the signal is applied intermittently, the signal is applied for a specific amount of time per day. In certain such embodiments, the signal is applied for about 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified duration.

In certain embodiments wherein the controller causes the signal to be applied intermittently, the signal is applied only when the subject is in a specific physiological state. For example, in certain embodiments, the signal may be applied only when the subject is asleep, and/or only when the subject is undergoing an apnoeic episode.

In certain such embodiments, the apparatus further comprises a communication, or input, element via which the status of the patient (e.g. that they are going to sleep) can be indicated by the patient or a physician. In alternative embodiments, as the apparatus further comprises a detector configured to detect the status of the patient, wherein the signal is applied only when the detector detects that the patient is in the specific state.

In certain embodiments, the one or more detected physiological parameters are selected from: sympathetic tone, duration of apnoeic episodes, frequency of apnoeic episodes, blood pressure, respiratory rate, tidal volume, upper airway resistance, blood oxygen level, blood $CO_2$ level, alveolar-arterial gradient (A-a gradient), disordered breathing index (DBI), and diaphragmatic muscle activity.

In certain embodiments, the one or more detected physiological parameters comprise an action potential or pattern of action potentials in a nerve of the patient, wherein the action potential or pattern of action potentials is associated with sleep apnoea. In certain such embodiments, the nerve is a renal nerve.

It will be appreciated that any two or more of the indicated physiological parameters may be detected in parallel or consecutively. For example, in certain embodiments, the controller is coupled to a detector or detectors configured to detect the pattern of action potentials in a nerve and also to detect the blood oxygen level.

In certain embodiments, the detector detects that the patient or subject is undergoing an apnoeic episode characterised by one or more physiological parameters being at or beyond the threshold value for each parameter. The detector then communicates with the controller which causes the signal to be applied as configured to do so.

In certain embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the methods, the increase in neural activity caused by the application of the signal is temporary. That is, upon cessation of the signal, neural activity in the nerve or nerves returns substantially towards baseline neural activity within about 1-60 seconds, or within about 1-60 minutes, for example within about 5 minutes, or within about 1-24 hours, optionally about 1-12 hours, optionally about 1-6 hours, optionally about 1-4 hours, optionally about 1-2 hours. In certain such embodiments, the neural activity returns substantially fully to baseline neural activity. That is, the neural activity following cessation of the signal is substantially the same as the neural activity prior to the signal being applied—i.e. prior to modulation. In certain alternative embodiments, the neural activity returns to a baseline neural activity that may be different from the neural activity prior to stimulation.

As demonstrated herein, the renal nerve can be stimulated such that the physiological effects of stimulation are temporary. That is, the change in one or more physiological parameters such as respiration rate, diaphragmatic contraction, tidal volume and blood pressure induced by renal nerve stimulation is exhibited only during and shortly after stimulation. In such embodiments, upon cessation of stimulation, the one or more physiological parameters change to a level different to the level exhibited during stimulation. In certain preferred embodiments, the one or more physiological parameters return to baseline (i.e. pre-stimulation) levels upon cessation of stimulation. This may be advantageous, for example, when treating conditions with transient or intermittent symptoms. For instance, application of the stimulation during an acute apnoeic episode can treat the condition without the effects of stimulation impacting on normal respiration. Therefore, in certain embodiments, the effect on a physiological parameter of renal nerve stimulation is temporary. In certain such embodiments, the physiological parameter returns to baseline level within 10 minutes, optionally within 5 minutes of signal cessation, optionally within 2 minutes, optionally within about 60 s of signal cessation.

In certain alternative embodiments, the increase in neural activity caused by the application of the signal is substantially persistent. That is, upon cessation of the signal, neural activity in the nerve or nerves remains substantially the same as when the signal was being applied—i.e. the neural activity during and following stimulation is substantially the same.

In certain embodiments, the increase in neural activity caused by the application of the signal is partially corrective, preferably substantially corrective. That is, upon cessation of the signal, neural activity in the nerve more closely resembles the pattern of action potentials observed in a healthy subject than prior to modulation, preferably substantially fully resembles the pattern of action potentials observed in a healthy subject. In such embodiments, upon cessation of the signal, the pattern of action potentials in the nerve or nerves resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

As is known by the skilled person, mammals have a left and a right renal nerve. Therefore, in certain embodiments, the signal is applied bilaterally. That is, in such embodiments, the signal is applied to a renal nerve on both the left and right side of the patient such that the neural activity is stimulated in the nerves to which the signal is applied—i.e. the modulation is bilateral. In such embodiments, the signal applied to each nerve, and therefore the extent of stimulation is independently selected from that applied to the other nerve or nerves. In certain embodiments the signal applied to the right nerve is the same as the signal applied to the left nerve. In certain alternative embodiments the signal applied to the right nerve is different to the signal applied to the left nerve.

In certain alternative embodiments, the signal is applied unilaterally—that is, to the right nerve only, or to the left nerve only.

In certain embodiments wherein the modulation is bilateral, each signal is applied by a neuromodulation device comprising one or more transducers for applying the signal. In certain such embodiments, all signals are applied by the same neuromodulation device, that device have at least two transducers, one to apply the signal to the left nerve and one to apply the signal to the right nerve. In certain alternative embodiments, each signal is applied by a separate neuromodulation device.

In those embodiments in which the signal is applied bilaterally, embodiments described herein apply equally and independently to the signal applied to the left nerve and to the right nerve unless indicated otherwise.

In certain embodiments of the methods according to the invention, the signal applied is an electrical signal, an electromagnetic signal (optionally an optical signal), a mechanical (optionally ultrasonic) signal, a thermal signal, a magnetic signal or any other type of signal.

In certain embodiments in which the signal is applied by a neuromodulation device comprising at least one transducer, the transducer may be comprised of one or more electrodes, one or more photon sources, one or more ultrasound transducers, one more sources of heat, or one or more other types of transducer arranged to put the signal into effect.

In certain embodiments, the signal applied is an electrical signal, for example a voltage or current. In those embodiments in which the signal is an electrical signal applied by a neuromodulation device comprising a transducer, the transducer is an electrode configured to apply the signal.

In certain embodiments the electrical signal applied comprises a direct current (DC) waveform, such as a charge balanced direct current waveform, or an alternating current (AC) waveform, or both a DC and an AC waveform.

In certain embodiments, the DC waveform or AC waveform may be a square, sinusoidal, triangular or complex waveform. The DC waveform may alternatively be a constant amplitude waveform. In certain embodiments the electrical signal is a DC square waveform, optionally of varying voltage.

It will be appreciated by the skilled person that the current/voltage of an applied electrical signal necessary to achieve the intended voltage/current stimulation (respectively) will depend upon the positioning of the electrode and the associated electrophysiological characteristics (e.g. impedance). It is within the ability of the skilled person to determine the appropriate current/voltage for achieving the intended stimulation in a given subject. For example, the skilled person is aware of methods suitable to monitor the neural activity profile induced by neuronal or nerve stimulation.

In certain embodiments, the electrical signal has a frequency of about 0.5-50 Hz, optionally of about 0.5-25 Hz, optionally about 1-10 Hz, optionally about 1-5 Hz. In certain embodiments, the electrical signal has a frequency of about 2-25 Hz, about 2-10 Hz, about 2-5 Hz or about 2-2.5 Hz. In certain preferred embodiments, the electrical signal has a frequency in the range of about 1 Hz to about 10 Hz, more preferably from about 2 Hz to about 5 Hz. In certain preferred embodiments, the electrical signal has a frequency in the range of from about 5 Hz to about 10 Hz.

In certain embodiments, the signal is an electrical signal having a frequency of at least about 2 Hz, optionally at least about 2.5 Hz. In certain embodiments the signal has a frequency of at least about 5 Hz.

In certain embodiments, the signal is an electrical signal having a frequency of about 2 Hz, about 2.5 Hz or about 5 Hz.

In certain embodiments, the signal is an electrical signal having a voltage of about 1-20V. In certain preferred embodiments, the signal has a voltage of about 5-15V, optionally about 10-15V. In certain embodiments, the signal is an electrical signal having a voltage of at least about 14V. In certain preferred embodiments the voltage is about 14V.

In certain embodiments, the signal is an electrical signal having a current of about 0.01-2 mA, optionally about 0.05-1 mA, optionally about 0.075-0.5 mA, optionally 0.1-0.5 mA. In certain embodiments, the signal has a current in the range of from about 0.08-0.15 mA.

In certain embodiments, the signal is an electrical signal having a current of at least about 0.01 mA, at least about 0.02 mA, at least about 0.03 mA, at least about 0.04 mA, at least about 0.05 mA, at least about 0.06 mA, at least about 0.07 mA, at least about 0.08 mA, at least about 0.09 mA, at least about 0.1 mA. In certain embodiments, the signal is an electrical signal having a current of at least about 0.3 mA, optionally at least about 0.5 mA.

In certain embodiments, the signal is an electrical signal having a current of about 0.1 mA. In certain embodiments, the signal is an electrical signal having a current of about 0.3 mA. In certain embodiments, the signal is an electrical signal having a current of about 0.5 mA.

In certain embodiments the signal is an electrical signal having a pulse width of about 0.1-5 ms, optionally about 0.1-2 ms, optionally about 0.2-1 ms, optionally about 0.5 ms. In certain embodiments the signal is an electrical signal and the signal has a pulse duration of less than or equal to about 1 ms, optionally less than or equal to about 0.9 ms, optionally less than or equal to about 0.8 ms, optionally less than or equal to about 0.7 ms, optionally less than or equal to about 0.6 ms, optionally less than or equal to about 0.5 ms. In certain embodiments the signal is an electrical signal having a pulse width of about 0.5 ms.

In certain preferred embodiments, the signal comprises a DC waveform, optionally a square waveform, of about 0.1 mA, 0.3 mA or 0.5 mA, and about 0.5 ms pulse width, with a frequency of at least about 2 Hz, at least about 2.5 Hz. In certain embodiments, the signal has a frequency of from about 2 Hz to about 5 Hz, optionally from about 2 Hz to about 2.5 Hz. In certain such embodiments, the signal has a frequency of about 2 Hz, about 2.5 Hz, or about 5 Hz.

In those embodiments in which the electrical signal is applied by a neuromodulation device comprising an electrode, the electrode may be a cuff or wire electrode. In certain embodiments, the electrode is bipolar or tripolar.

In a fourth aspect, the invention provides a neuromodulatory electrical waveform for use in treating sleep apnoea in a patient, wherein the waveform is an alternating current (AC) or direct current (DC) waveform having a frequency of about 0.5-50 Hz, optionally 0.5-25 Hz, optionally 1-10 Hz, optionally 1-5 Hz, optionally 2-2.5 Hz, such that, when applied to renal nerve the waveform stimulates neural signalling in the nerve. In certain embodiments, the waveform, when applied to the nerve, relieves or prevents sleep apnoea.

In a fifth aspect, the invention provides use of a neuromodulation device as described herein for treating sleep apnoea in a patient by stimulating neural activity in a renal nerve of the patient.

In a sixth aspect, the invention provides a neuromodulation system, the system comprising a plurality of devices according to the first aspect. In such a system, each device may be arranged to communicate with at least one other device, optionally all devices in the system. In certain embodiments, the system is arranged such that, in use, the devices are positioned to bilaterally stimulate the neural activity in the afferent fibres of the renal nerves of a patient.

In such embodiments, the system may further comprise additional components arranged to communicate with the devices of the system, for example a processor, a data input facility, and/or a data display module. In certain such embodiments, the system further comprises a processor. In certain such embodiments, the processor is comprised within a mobile device (for example a smart phone) or computer.

In a preferred embodiment of all aspects of the invention, the subject or patient is a mammal, more preferably a human.

In a preferred embodiment of all aspects of the invention, the signal or signals is/are applied substantially exclusively to the nerves specified, and not to other nerves.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

The present inventors identified that the renal nerve could represent an effective axis via which to treat sleep apnoea. This hypothesis was investigated and demonstrated as set out in the following examples.

Example 1

Loss of Renal Afferent Input Elicits Markedly Disordered Breathing

Methods

All studies used adult male Sprague-Dawley rats of 12-14 weeks of age. Bilateral renal nerve transection was performed as per Foss et al., Am J Physiol Regul Integr Comp Physiol. 308: R112-R122, 2015 (incorporated herein by reference). Bilateral dorsal root ganglionectomy (Left T10-L1, Right T9-T13) were performed as per Lappe et al., Am J Physiol. 249: R634-R637, 1985 (incorporated herein by reference). Bilateral application of vehicle or capsaicin to the renal nerves was performed as per Foss et al., 2015. A piece of gauze soaked in a capsaicin solution (33 mM in 5% ethanol, 5% Tween 80 and 90% saline) was wrapped around the renal artery and vein for 15 min. A piece of parafilm was placed under the renal artery and vein prior to placement of capsaicin-soaked gauze to prevent non-renal capsaicin exposure. After 15 min of capsaicin exposure, the gauze and parafilm were removed, the area was dried, and the procedure was repeated on the contralateral side. All rats used in the above studies were allowed 7 days to recover from surgeries before use.

Results

As seen in FIG. 3, increases in disordered breathing index (DBI, also referred to as disrupted breaths (DR)) during light and dark cycles results from (1) bilateral renal nerve transection (RLNX), (2) bilateral removal of DRG that contain renal afferent cell bodies (DRGX), or (3) bilateral application of capsaicin to the renal nerves to destroy small diameter unmyelinated C-fibre afferents (CAPX). DBI was determined by identifying apnoeas, type 1 and type 2 sighs shown on each animal's breathing traces.

The increases in DBI were due to prevalence of apnoeas. Specifically, increased number and durations of apnoeas accounted for (1) 86±9% of enhanced DBI in RLNX rats, (2) 91±9% of enhanced DBI in DRGX rats, and (3) 72±9% of the enhanced DBI in CAPX rats.

Example 2

Renal Afferent Nerve Stimulation Diminishes Disordered Breathing

Example 2a

Since transection of the renal nerves elicited an increase in disordered breathing index (DBI) (see Example 1)) it was hypothesized that electrical stimulation of renal afferents may have the ability to diminish the expression and frequency of disordered breathing including apnoeas in freely-moving rats.

Methods

All studies used adult male Sprague-Dawley rats of 12-14 weeks of age. The main renal nerve from the left kidney was isolated and placed in a cuffed platinum bipolar electrode for subsequent electrical stimulation in the freely-moving state (Lewis et al., Hypertension 13: 759-765, 1989, incorporated herein by reference). In some rats, the ipsilateral left DRG (T10-L1) were surgically removed. All rats used were allowed 3 days to recover from surgeries before use in experiments. On the day of study, the nerves were stimulated at 2 Hz (14 V, 0.5 ms) for 30 sec per stimulus followed by 30 sec of rest continuously beginning at 4 pm (1600 h) until 8 am (0800 h).

Results

As seen in FIG. 4 (top left panel), electrical stimulation of the left renal nerve (L-RNS) (2 Hz, 14 V, 0.5 ms for 30 sec/stimulus followed by 30 sec of rest continuously throughout the cycle) did not impact the frequency of breathing in freely-moving rats during the light or dark cycles (top-left panel). In contrast, L-RNS elicited a pronounced reduction in DBI (bottom-left panel of FIG. 4). The majority of circadian cycle-induced increase in DBI in sham-operated rats was due to higher incidence and duration of apnoeas, the incidence of which were decreased by (73±8%, P±0.05) in rats that received L-RNS.

As seen in the right-hand panels of FIG. 4, L-RNS did not affect frequency of breathing or the degree disordered breathing in rats in which the ipsilateral DRG that house the vast majority of renal afferent cell bodies were removed.

Example 2b

Based upon the above findings, we sought more evidence that electrical stimulation of renal afferents can decrease disordered breathing. We hypothesized that electrical stimulation of renal afferents would diminish the increase in the disordered breathing index (DBI) that occurs in freely-moving rats upon return to room-air after a hypoxic-hypercapnic episode (May et al., Open J Mol Integ Physiol. 3: 134-145, 2013, incorporated herein by reference).

Methods

All studies used adult male Sprague-Dawley rats of 12-14 weeks of age. The main renal nerves from the left and right kidneys were isolated and placed in cuffed platinum bipolar electrodes for the subsequent electrical stimulation in freely-moving rats [Lewis et al., 1989]. All rats were allowed 3 days to recover. The rats were placed in whole-body plethysmography chambers to monitor ventilation and disordered breathing index (DBI) [May et al., 2013; Getsy et al., Respir Physiol Neurobiol. 204: 147-59, 2014, incorporated herein by reference]. The rats were exposed to a hypoxic-hypercapnic challenge [rats rebreathed their own air; May et al., 2013] and then immediately upon return to room-air, both renal nerves were stimulated for 5 min (2.5 Hz, 0.1 mA, 0.5 msec).

Results

As seen in FIG. 5, the hypoxic-hypercapnic challenge elicited a gradually occurring increase in frequency of breathing whereas the return to room-air elicited a period of ventilatory excitation known as Short-Term Potentiation (STP). As also seen in FIG. 5, the occurrence of disordered breathing (DR breaths)—defined by the number of apnoeas, sighs and sniffs [see Strohl et al., Compr Physiol. 2: 1853-

1872, 2012, incorporated herein by reference] decreased during the hypoxic-hypercapnic challenge whereas disordered breathing rose markedly upon return to room-air. The major finding was that whereas the tachypnea upon return to room-air was not affected by 5 min of 2.5 Hz electrical stimulation of both renal nerves given immediately upon return to room-air, this stimulation markedly affected the magnitude of disordered breathing. The effect was most evident during the period of stimulation and for about 5 min after cessation of the stimulation.

Example 3

Intra-Renal Artery Infusion of Capsaicin Greatly Diminishes Disordered Breathing Since the loss of small diameter renal C-fibres elicited an increase in disordered breathing index (DBI, see Example 1) we hypothesized that activation of these afferents via infusion of capsaicin into the renal artery may diminish expression of disordered breathing including apnoeas in freely-moving rats.

Methods

All studies used adult male Sprague-Dawley rats of 12-14 weeks of age. A PE-10 catheter stretched at the tip was implanted into the left supra-renal artery to allow continuous infusion of vehicle (1% Tween 80, 1% ethanol, and 98% saline; at 1 µL/min) or capsaicin (1 µg/kg/min) as per Smits and Brody, Am J Physiol. 247: R1003-R1008, 1984, incorporated herein by reference. In some rats, the ipsilateral left DRG (T10-L1) were surgically removed. All rats had 3 days to recover before use. On the day of the study, vehicle or capsaicin infusions were administered every alternate minute continuously beginning at 4 pm (1600 h) all the way through until 8 am (0800 h).

Results

As can be seen in FIG. 6, intra-renal artery infusion of capsaicin elicited a minor increase in the frequency of breathing (about 8 breaths/min) during the light or dark cycles of freely-moving rats (top-left panel). This response was absent in rats in which the ipsilateral DRG that house the majority of renal afferent cell bodies were removed (top-right panel). In contrast, infusion of capsaicin elicited a pronounced reduction in the disordered breathing index (DBI) (bottom-left panel). The majority of circadian cycle-induced increase in DBI in sham-operated rats was due to higher incidence and duration of apnoeas the incidence of which were decreased by (82±8%, P<0.05) in rats that received capsaicin.

As seen in the bottom-right had panel of FIG. 6, the infusion of capsaicin did not affect DBI in rats in which the ipsilateral DRG were removed.

Example 4

Renal Nerve Stimulation Decreases Airway Resistance in Zucker-Fat Rats

The ability of renal afferents to open the airways would be of obvious benefit to patients with sleep apnoea, especially obstructive sleep apnoea [Dempsey et al., Physiol Rev. 90: 47-112, 2010, incorporated herein by reference]. Based on electrophysiological findings [Felder, Am J Physiol. 250: R580-R588, 1986, incorporated herein by reference], we hypothesize renal afferent input will recruit brainstem circuits that ultimately lead to opening of obstructed airways.

Zucker-fat rats are obese and type 2 diabetic and display night-time hypertension [Dempsey et al., 2010; Fellmann et al., Pharmacol Ther. 137: 331-340, 2013; Wang et al., Curr Diabetes Rev. 10:131-145, 2014, all of which are incorporated herein by reference] and suffer from neuropathic pain [Gao and Zheng, Exp Clin Endocrinol Diabetes 122: 100-106, 2014, incorporated herein by reference]. Zucker-fat rats are an accepted model of human sleep apnoea [Iwasaki et al., Heart Rhythm 9: 1409-1416, 2012, incorporated herein by reference] and studies by the inventors provide unequivocal evidence that Zucker-fat rats have key hallmarks of sleep apnoea. Specifically, they provide direct evidence for the occurrence of apnoeic episodes during sleep and considerable evidence for other manifestations of sleep apnoea such as day-time hypercapnia and awake-sleep cycle-dependent abnormalities in response to hypoxic-hypercapnic challenges.

Methods

All studies used adult male Zucker-Fat rats of 15-17 weeks of age. The rats were prepared for bilateral electrical stimulation of both renal nerves and allowed 4 days to recover from surgery [Lewis et al., 1989]. On the day of the study, the rats were placed in head-out double-chamber plethysmography chambers to continuously monitor airway resistance [Renninger, Curr Protoc Pharmacol. Chapter 10: Unit 10.11, 2006; Ewert et al., J Pharmacol Toxicol Methods 61: 219-229, 2010, incorporated herein by reference]. The rats were challenged with four Hypoxic-Hypercapnic (H—H) gas challenges (10% $O_2$, 5% $CO_2$, 15% $N_2$) for 3 min separated by 15 min. The renal nerve stimulators were turned on at beginning of H—H challenge and continued for 3 min afterwards during the peak of the post-HH increases in airway resistance. Bilateral renal nerve stimulation parameters were 2.5 Hz (0.1 mA, 0.5 msec) for 6 minutes— 45 sec on 15 sec off.

Results

As can be seen in FIG. 7, the HH challenges did not affect airway resistance (Sraw) whereas Sraw rose markedly upon return to room air (far left and far right panels). Moreover, stimulation of the renal nerves actively decreased Sraw during and following exposure to HH challenges (middle panels). As such, this novel finding suggests that renal afferent input controls airway patency in Zucker-fat rats and that stimulation of the renal nerve can alleviate upper airway restriction.

Example 5

Renal Nerve Stimulation Increases Respiratory Drive in Anaesthetised Zucker-Fat Rats Methods Male Zucker Fat rats (630-840 g, 4-6 months old) were anaesthetised with 50 mg/kg intraperitoneal injection of sodium pentobarbital and maintained with an intravenous infusion of 10 mg/kg/hr sodium pentobarbital into the right femoral vein. Mean arterial blood pressure and heart rate were measured via an intravenous cannula into the right carotid artery. Leads were placed on the diaphragm to measure diaphragmatic EMG and record peak changes in breathing. An algorithm that calculates the number of peaks per minute was applied on the integrated diaphragmatic EMG activity to calculate respiratory rate. A bipolar electrode was placed around the left renal nerve and stimulation delivered using a grass stimulator.

Results

The representative trace in FIG. 8 demonstrates a stimulus dependent increase in diaphragmatic EMG, air flow, respiration rate and heart rate but a stimulus evoked decrease in mean arterial blood pressure. As seen in FIG. 9 renal afferent stimulation (2.5 Hz, 0.5 ms, 0.5 mA, 30 seconds and 5 Hz, 0.5 ms, 0.5 mA, 30 seconds) increased both respiration rate (35%±15 and 50%±11 for 2.5 Hz and 5 Hz, respectively) and the frequency and force of diaphragmatic contraction, as measured by an increase (26%±10 and 37%±27 for 2.5 Hz and 5 Hz, respectively) in the area under the curve of diaphragmatic EMG. The increase of diaphragmatic EMG and respiration rate resulted in an increase of 40%±30 and 69%±16 for 2.5 Hz and 5 Hz, respectively, in air flow. Renal afferent stimulation elicited a decrease of 10%±8 and 24%±4 for 2.5 Hz and 5 Hz, respectively, in mean arterial blood pressure. A concurrent increase in heart rate (5%±3 and 6%±4 for 2.5 Hz and 5 Hz, respectively) was also observed upon renal afferent stimulation. All measured parameters returned to within 5% of pre-stimulation levels within 60 seconds cessation of stimulation.

CONCLUSIONS

Our findings clearly show that renal afferents including small diameter unmyelinated C-fibre afferents play an important role in the expression of disordered breathing in freely-moving rats.

The findings that electrical stimulation of renal afferents decreases disordered breathing indices and particularly the expression of apnoeas, suggests that such renal nerve stimulation may be an effective therapeutic strategy for the treatment of breathing irregularities, in particular sleep apnoea.

The findings that removal of DRG that contain the cell bodies of renal afferents results in loss of the reduction in disordered breaths elicited by renal nerve stimulation suggests that the reduction in disordered breaths is mediated via the renal afferent fibres. In addition, the selective destruction of renal small diameter unmyelinated C-fibre afferents results in enhanced expression of disordered breathing and especially apnoeas, suggesting that the renal nerve influence on respiratory behaviour is mediated via the afferent C fibres.

The fact that renal afferent stimulation evoked an increase in diaphragmatic EMG demonstrates activation of a central reflex where regions within the brain and/or spinal cord are activated, corroborating neuronal tracing studies by Wyss and Donovan (Wyss, J. M., and M. K. Donovan. A direct projection from the kidney to the brainstem. Brain Res. 298: 130-134, 1984, incorporated herein by reference).

Activation of central nuclei drives an increase in phrenic efferent nerve activity resulting in an increase in diaphragmatic EMG, thus improving central drive to breathe. The increase in diaphragmatic EMG drives the increase in airflow or tidal volume.

Improvements in central drive to breathe will be useful in treating conditions such as central and/or obstructive sleep apnoea and other conditions where there is an impairment in central drive to breathe.

The invention claimed is:

1. A neuromodulation apparatus for stimulating neural activity in a renal nerve of a human subject for producing a physiological response, the apparatus comprising:
   at least two electrodes configured to intermittently apply electrical signals to a renal nerve of the human subject; and
   a controller coupled to the at least two electrodes, the controller controlling the electrical signals to be applied by the at least two electrodes, such that the electrical signals temporarily increase neural activity in the renal nerve to produce the physiological response in the human subject for treating sleep apnea in the human subiect, wherein the physiological response is an improvement in one or more physiological parameters selected from: duration of apneic episodes, frequency of apneic episodes, heart rate, respiratory rate, tidal volume, upper airway resistance, blood oxygen level, blood $CO_2$ level, alveolar-arterial gradient, disordered breathing index, and diaphragmatic muscle activity,
   wherein the electrical signals comprise an alternating current (AC) waveform and/or a DC waveform.

2. The apparatus according to claim 1, wherein at least one of the signals has a frequency of from 0.5 to 50 Hz.

3. The apparatus according to claim 1, wherein at least one of the signals has a voltage of 1-20V.

4. The apparatus according to claim 1, wherein at least one of the signals has a current of 0.01-2 mA.

5. The apparatus according to claim 1, wherein at least one of the signals has a pulse width of 0.1-5 ms.

6. The apparatus according to claim 1, wherein at least one of the signals has a pulse width of less than or equal to 1 ms.

7. The apparatus according to claim 1, wherein at least one of the signals comprises a DC waveform of 0.1 mA and 0.5 ms pulse width, with a frequency of about 2-5 Hz.

8. The apparatus according to claim 1, wherein the apparatus further comprises a detector element to detect one or more physiological parameters in the human subiect, wherein the controller is coupled to said detector element, and causes one of the at least two electrodes to apply an electrical signal when the physiological parameter is detected to be meeting or exceeding a predefined threshold value, wherein one or more of the detected physiological parameters is selected from: duration of apneic episodes, frequency of apneic episodes, heart rate, respiratory rate, tidal volume, upper airway resistance, blood oxygen level, blood $CO_2$ level, alveolar-arterial gradient, disordered breathing index, and diaphragmatic muscle activity.

9. A method of treating sleep apnea in a human subject comprising:
   i. implanting in the human subject the apparatus according to claim 4;
   ii. positioning the at least two electrodes of the apparatus in signaling contact with a renal nerve of the human subject; and
   iii. activating the apparatus.

10. A method of treating sleep apnea -in a human subject, the method comprising intermittently applying a signal to a renal nerve of said human subject to temporarily increase neural activity in the renal nerve in the human subject and produce a physiological response indicative of treating sleep apnea -in the human subject, wherein the signal is applied by a neuromodulation apparatus comprising at least two transducers configured to apply the signal, wherein treatment for sleep apnea is indicated by the physiological response being an improvement in one or more measurable physiological parameters selected from: duration of apneic episodes, frequency of apneic episodes, respiratory rate, tidal volume, upper airway resistance, blood oxygen level, blood $CO_2$ level, alveolar-arterial gradient, disordered breathing index, and diaphragmatic muscle activity.

11. The method according to claim 10, wherein the signal is an electrical signal, and when the signal is applied by a neuromodulation apparatus, the one or more transducers configured to apply the signal is an electrode.

12. The method according to claim 11, wherein the signal has a frequency of from 0.5 to 50 Hz.

13. The method according to claim 11, wherein the signal has a voltage of 1-20V.

14. The method according to claim 11, wherein the signal has a current of 0.01-2 mA.

15. The method according to claim 11, wherein the signal has a pulse width of 0.1-5 ms.

16. The method according to claim 11, wherein the signal has a pulse width of less than or equal to 1 ms.

17. The method according to claim 10, wherein a first signal is applied to a left renal nerve and a second signal is applied to a right renal nerve of the human subject.

18. The method according to claim 17, wherein the first signal is applied by a first neuromodulation apparatus and the second signal is applied by a second neuromodulation apparatus.

* * * * *